US010876038B2

(12) United States Patent
Weerasooriya et al.

(10) Patent No.: US 10,876,038 B2
(45) Date of Patent: Dec. 29, 2020

(54) SHORT HYDROPHOBE ANIONIC SURFACTANTS

(71) Applicant: BOARD OF REGENTS, THE UNIVERSITY OF TEXAS SYSTEM, Austin, TX (US)

(72) Inventors: Upali P. Weerasooriya, Austin, TX (US); Gary A. Pope, Cedar Park, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/066,386

(22) Filed: Mar. 10, 2016

(65) Prior Publication Data

US 2016/0264847 A1     Sep. 15, 2016

Related U.S. Application Data

(60) Provisional application No. 62/131,138, filed on Mar. 10, 2015.

(51) Int. Cl.
*C09K 8/584* (2006.01)
*C07C 59/125* (2006.01)
*C07C 305/06* (2006.01)

(52) U.S. Cl.
CPC ............ *C09K 8/584* (2013.01); *C07C 59/125* (2013.01); *C07C 305/06* (2013.01)

(58) Field of Classification Search
None
See application file for complete search history.

(56) References Cited

U.S. PATENT DOCUMENTS

| 8,684,080 | B2* | 4/2014 | Bittner | C09K 8/584 |
| | | | | 166/270.1 |
| 2009/0264598 | A1* | 10/2009 | Bittner | B01F 17/0021 |
| | | | | 525/231 |
| 2010/0282467 | A1* | 11/2010 | Hutchison | C07C 303/06 |
| | | | | 166/305.1 |
| 2011/0220353 | A1* | 9/2011 | Bittner | C09K 8/588 |
| | | | | 166/270.1 |
| 2013/0281327 | A1* | 10/2013 | Weerasooriya | C09K 8/584 |
| | | | | 507/202 |

FOREIGN PATENT DOCUMENTS

| WO | 2008/012242 A1 | 1/2008 |
| WO | 2009/100298 A1 | 8/2009 |
| WO | 2013/040313 | 3/2013 |

OTHER PUBLICATIONS

Third Party Observation, dated Dec. 23, 2016, received in connection with International Patent Application No. PCT/US16/21729.
International Search Report and Written Opinion, dated May 27, 2016, received in connection with International Patent Application No. PCT/US16/21729.

* cited by examiner

*Primary Examiner* — Jeffrey D Washville
(74) *Attorney, Agent, or Firm* — Meunier Carlin & Curfman LLC

(57) ABSTRACT

Provided herein are compounds, compositions, and methods having application in the field of enhanced oil recovery (EOR). In particular, the short hydrophobe anionic surfactants as well as aqueous compositions comprising these surfactants are provided that can be used for the recovery of a large range of crude oil compositions from challenging reservoirs.

25 Claims, 7 Drawing Sheets

SHORT HYDROPHOBE ANIONIC SURFACTANTS

CROSS REFERENCE TO RELATED APPLICATIONS

This application claims the benefit of U.S. Provisional Application No. 62/131,138, filed Mar. 10, 2015, which is incorporated herein by reference in its entirety.

BACKGROUND

Enhanced Oil Recovery (EOR) refers to techniques for increasing the amount of unrefined petroleum, or crude oil that may be extracted from an oil reservoir (e.g., an oil field). Using EOR, 40-60% of the reservoir's original oil can typically be extracted compared with only 20-40% using primary and secondary recovery (e.g., by water injection or natural gas injection). Enhanced oil recovery may also be referred to as improved oil recovery or tertiary oil recovery (as opposed to primary and secondary oil recovery).

Enhanced oil recovery may be achieved by a variety of methods including miscible gas injection (which includes carbon dioxide flooding), chemical injection (which includes polymer flooding, alkaline flooding, and surfactant flooding), microbial injection, or thermal recovery (which includes cyclic steam, steam flooding, and fire flooding). The injection of various chemicals, usually as dilute aqueous solutions, has been used to improve oil recovery. Injection of alkaline or caustic solutions into reservoirs with oil that has organic acids naturally occurring in the oil (also referred to herein as "unrefined petroleum acids") will result in the production of soap that may lower the interfacial tension enough to increase production. Injection of a dilute solution of a water soluble polymer to increase the viscosity of the injected water can increase the amount of oil recovered from geological formations. Aqueous solutions of surfactants such as petroleum sulfonates may be injected to lower the interfacial tension or capillary pressure that impedes oil droplets from moving through a reservoir. Special formulations of oil, water and surfactant microemulsions have also proven useful. Such formulations often include co-solvent compounds to increase the solubility of the solutes in the presence of oil and decrease the viscosity of an emulsion. However, co-solvents typically have the undesirable consequence of also increasing interfacial tension. Further, application of these methods is usually limited by the cost of the chemicals and their adsorption and loss onto the rock of the oil containing formation.

Therefore, there is a need in the art for cost effective methods for enhanced oil recovery using chemical injection. Provided herein are methods and compositions addressing these and other needs in the art.

SUMMARY

Provided herein are short hydrophobe anionic surfactants. The short hydrophobe anionic surfactants can be defined by Formula I below Formula I

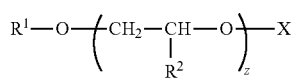

wherein $R^1$ is a $C_7$-$C_{12}$ alkyl group, an $R^3$-substituted aryl group, or an $R^3$-substituted cycloalkyl group; $R^2$ is independently hydrogen or methyl; $R^3$ is an alkyl group, wherein the alkyl group together with the aryl group or cycloalkyl group to which the alkyl group is attached comprise from 7 to 12 carbon atoms; z is an integer from 2 to 24 (e.g., an integer from 2 to 15); X is —$SO_3^-M^+$, —$SO_3^H$, —$CH_2C(O)O^-M^+$, —$CH_2C(O)OH$; and $M^+$ is a cation. In certain embodiments, the short hydrophobe anionic surfactant can be a sulfate surfactant (e.g., X can be —$SO_3^-M^+$ or —$SO_3^H$). In certain embodiments, the short hydrophobe anionic surfactant can be a carboxylate surfactant (e.g., X can be —$CH_2C(O)O^-M^+$ or —$CH_2C(O)OH$). In certain embodiments, $R^1$ can be a branched $C_7$-$C_{12}$ alkyl group (e.g., a 2-ethylhexyl group or a 2-propylheptyl group).

In some cases, the short hydrophobe anionic surfactants can be defined by Formula II below Formula II

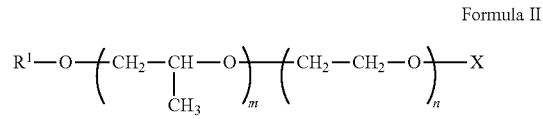

where $R^1$ is a $C_7$-$C_{12}$ alkyl group, an $R^3$-substituted aryl group, or an $R^3$-substituted cycloalkyl group; $R^3$ is an alkyl group, wherein the alkyl group together with the aryl group or cycloalkyl group to which the alkyl group is attached comprise from 7 to 12 carbon atoms; m is an integer from 2 to 24 and n is an integer from 0 to 22, with the proviso that m+n is from 2 to 24; X is —$SO_3^-M^+$, —$SO_3^H$, —$CH_2C(O)O^-M^+$, —$CH_2C(O)OH$; and $M^+$ is a cation. In some cases, m can be from 2 to 15 and/or n can be from 0 to 10. In certain cases, m can be an integer from 3 to 10 and n can be an integer from 0 to 10, and the sum of m and n (m+n) can be from 3 to 15. In certain embodiments, the short hydrophobe anionic surfactant can be a sulfate surfactant (e.g., X can be —$SO_3^-M^+$, —$SO_3^H$). In certain embodiments, the short hydrophobe anionic surfactant can be a carboxylate surfactant (e.g., X can be —$CH_2C(O)O^-M^+$, —$CH_2C(O)OH$). In certain embodiments, $R^1$ can be a branched $C_7$-$C_{12}$ alkyl group (e.g., a 2-ethylhexyl group).

The short hydrophobe anionic surfactants described herein can be used in EOR formulations to impart many beneficial properties generally afforded by co-solvents. For example, the short hydrophobe anionic surfactants can provide for faster equilibration, low microemulsion viscosity, and improved aqueous stability. In particular, the short hydrophobe anionic surfactants described herein can impart one or more of these desirable properties (e.g., lower microemulsion viscosity) without increasing interfacial tension (or do not decrease solubilization ratio). Thus, the short hydrophobe anionic surfactants described herein can be incorporated into EOR formulations to increase aqueous stability, speed up equilibration, broaden the low interfacial tension region, decrease microemulsion viscosity, reduce surfactant retention, and combinations thereof. As the short hydrophobe anionic surfactants described herein can exhibit the dual functions coming from a surfactant and a co-solvent in EOR formulations, the short hydrophobe anionic surfactants described herein can be used to develop/prepare EOR formulations that are free or substantially free from co-solvents (or that include decreased amounts of co-solvents). This can improve the efficiency of the EOR process since co-solvents also partition into excess water and oil phases and whereas surfactants stay almost entirely in the membrane phase.

Accordingly, also provided are formulations for use in EOR that comprise the short hydrophobe anionic surfactants described herein. For example, provided herein are aqueous compositions that comprise a short hydrophobe anionic surfactant described herein and an additional surfactant. The additional surfactant is also referred to herein as a "co-surfactant." In some cases, the short hydrophobe anionic surfactant and the additional surfactant can form a synergistic mixture with interfacial properties superior to either individual component. The short hydrophobe anionic surfactant and the additional surfactant can each independently be present in the composition in an amount of from 0.05% to 2% by weight, based on the total weight of the composition.

The additional surfactant can comprise any suitable single surfactant or a blend of one or more suitable surfactants. For example, the additional surfactant can comprise an anionic surfactant selected from the group consisting of alkoxy carboxylate surfactants, alkoxy sulfate surfactants, alkoxy sulfonate surfactants, alkyl sulfonate surfactants, aryl sulfonate surfactants, olefin sulfonate surfactants, and combinations thereof. In some cases, the additional surfactant can comprise a $C_{10}$-$C_{30}$ internal olefin sulfate (IOS) or a $C_8$-$C_{30}$ alkyl benzene sulfonate (ABS). In some cases, the additional surfactant can comprise an alkoxy carboxylate surfactant defined by Formula III or Formula IV

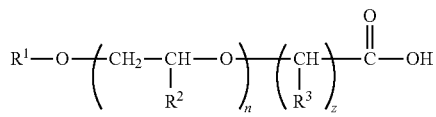

Formula III

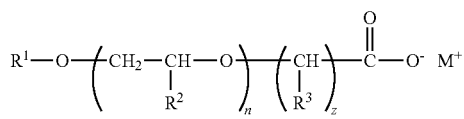

Formula IV wherein $R^1$ substituted or unsubstituted $C_8$-$C_{150}$ alkyl or substituted or unsubstituted aryl; $R^2$ is independently hydrogen or unsubstituted $C_1$-$C_6$ alkyl; $R^3$ is independently hydrogen or unsubstituted $C_1$-$C_6$ alkyl; n is an integer from 2 to 210; z is an integer from 1 to 6; and $M^-$ is a cation. In some cases, the additional surfactant can comprise an alkoxy sulfate surfactant defined by the formula below

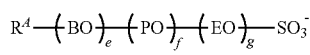

or acid or salt thereof, wherein $R^A$ is $C_8$-$C_{36}$ alkyl group; BO represents —$CH_2$—CH(ethyl)-O—; PO represents —$CH_2$—CH(methyl)-O—; EO represents —$CH_2$—$CH_2$—O—; and e, f and g are each independently integers from 0 to 50, with the proviso that at least one of e, f and g is not zero. In some embodiments, at least one of e and f is not zero. In some cases, the additional surfactant can comprise an alkoxy sulfate surfactant defined Formula VI

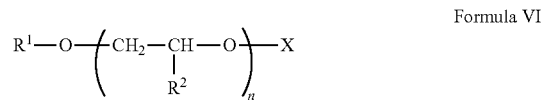

Formula VI wherein $R^1$ is an $R^4$-substituted or unsubstituted $C_8$-$C_{20}$ alkyl group, an $R^3$-substituted or unsubstituted aryl group, or an $R^3$-substituted or unsubstituted cycloalkyl group; $R^2$ is independently hydrogen or methyl; $R^3$ is independently an $R^4$-substituted or unsubstituted $C_1$-$C_{15}$ alkyl, an $R^4$-substituted or unsubstituted aryl group, or an $R^4$-substituted or unsubstituted cycloalkyl group; $R^4$ is independently an unsubstituted aryl group or an unsubstituted cycloalkyl group; n is an integer from 25 to 115; X is —$SO_3^-M^+$, —$SO_3^H$, —$CH_2C(O)O^-M^+$, —$CH_2C(O)OH$; and $M^+$ is a cation.

By way of example, in one embodiment, the aqueous composition can comprise (i) 0.05% to 1% by weight of the compound of any of claims 1-12; (ii) 0.05% to 1% by weight of a $C_{10}$-$C_{30}$ internal olefin sulfate (IOS) or a $C_8$-$C_{30}$ alkyl benzene sulfonate (ABS); and (iii) 0.05% to 1% by weight an alkoxy sulfate surfactant defined by the formula below

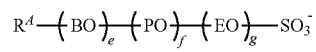

or acid or salt thereof, wherein $R^A$ is $C_8$-$C_{36}$ alkyl group; BO represents —$CH_2$—CH(ethyl)-O—; PO represents —$CH_2$—CH(methyl)-O—; EO represents —$CH_2$—$CH_2$—O—; and e, f and g are each independently integers from 0 to 50, with the proviso that at least one of e, f, and g is not zero.

The aqueous compositions can further include additional components including, by way of example, viscosity-enhancing water-soluble polymers, alkali agents, co-solvents, and combinations thereof. In certain embodiments, the composition can be substantially free of co-solvents (e.g., the composition can include less than 0.05% by weight co-solvents, based on the total weight of the composition).

Also provided are methods of using the short hydrophobe anionic surfactants and aqueous compositions described herein to displace an unrefined petroleum material in contact with a solid material. These methods can include, for example, methods of using the short hydrophobe anionic surfactants and aqueous compositions described herein in EOR. The methods can comprise (i) contacting the unrefined petroleum material with a short hydrophobe anionic surfactant described herein or an aqueous composition described herein, wherein the unrefined petroleum material is in contact with the solid material (e.g., to form an emulsion comprising the unrefined petroleum material); and (ii) allowing the unrefined petroleum material to separate from the solid material, thereby displacing the unrefined petroleum material in contact with the solid material. The solid material can comprise, for example, an endogenous solid material in a petroleum reservoir.

DETAILED DESCRIPTION

Definitions

Figure 1A:
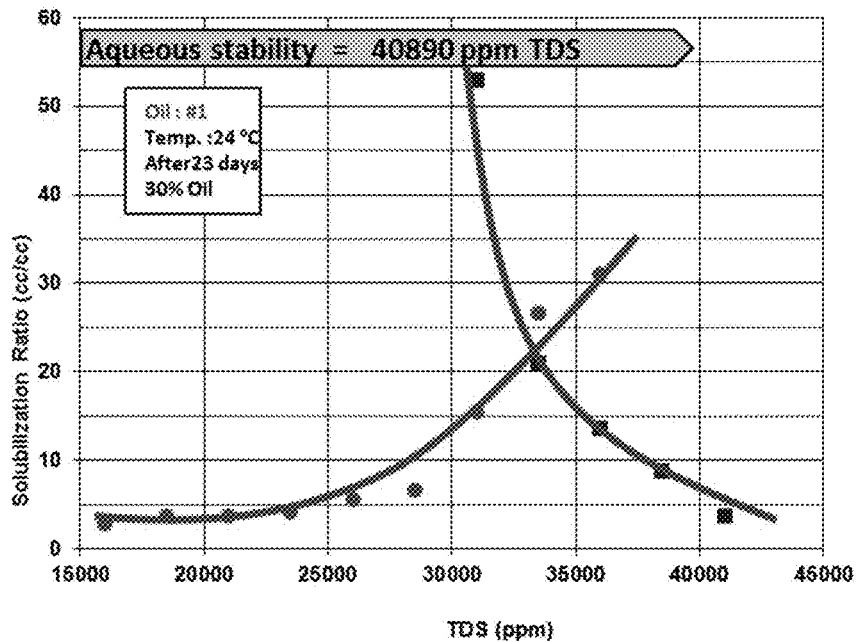
FIG. 1A is a plot of the solubilization ratios for light crude oil using a surfactant formulation that includes 0.55% TDA- 13PO-Sulfate, 0.2% C20-24 IOS, and 0.75% Phenol-2EO (1.5% total chemical content) with Oil #1 (30%) at 24° C. after 23 days. The arrow in the histogram pointing from left to right indicates the aqueous stability at 40,890 ppm (TDS) of $Na_2CO_3$.
Figure 1B:
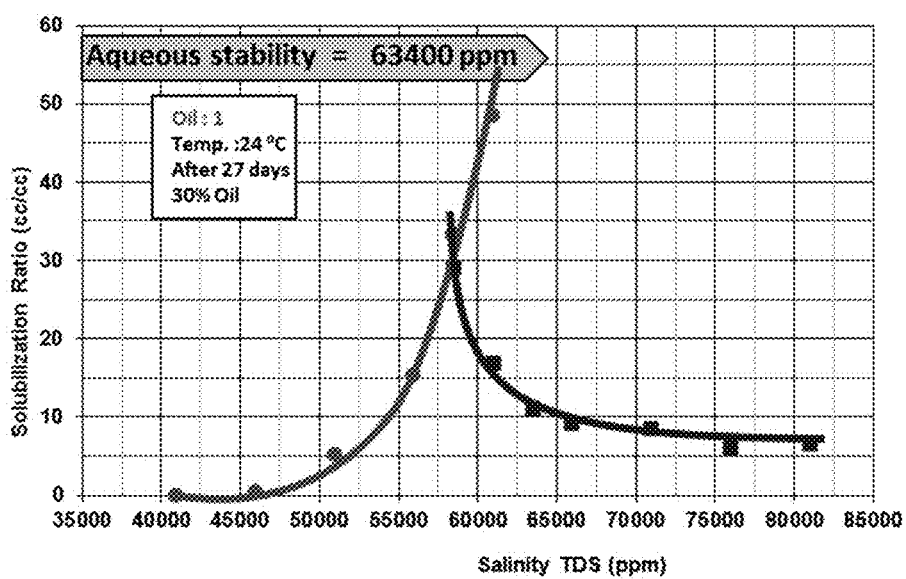
FIG. 1B is a plot of the solubilization ratios for light crude oil using a surfactant formulation that includes 0.1% TDA-13PO-Sulfate, 0.2% C20-24 IOS, 0.2% TDA-45PO-10EO-Sulfate, and 0.25% 2-Ethylhexanol-7PO-Sulfate (0.75% total chemical content) with Oil #1 (30%) at 24° C. after 27 days. The arrow in the histogram pointing from left to right indicates the aqueous stability at 63,400 ppm (TDS) of $Na_2CO_3$.

Unless otherwise indicated, the abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain which may be fully saturated, mono- or polyunsaturated (e.g., oleic, linoleic, and linolenic) and can include di- and multivalent radicals, having the number of carbon atoms designated (e.g., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, n-nonyl, n-decyl, n-undecyl, n-dodecyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl". An alkoxy is an alkyl attached to the remainder of the molecule via an oxygen linker (—O—).

The term "alkylene" by itself or as part of another substituent means a divalent radical derived from an alkyl, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred. A "lower alkyl"

or "lower alkylene" is a shorter chain alkyl or alkylene group, generally having eight or fewer carbon atoms.

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si and S, and wherein the nitrogen and sulfur atoms may optionally be oxidized and/or the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—OCH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— can represent both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The term "aryl" means, unless otherwise stated, a polyunsaturated, aromatic, hydrocarbon substituent which can be a single ring or multiple rings (preferably from 1 to 3 rings) which are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. Similarly, a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent means a divalent radical derived from an aryl and heteroaryl, respectively.

The term "oxo" as used herein means an oxygen that is double bonded to a carbon atom.

Where a substituent of a compound provided herein is "R-substituted" (e.g., $R^2$-substituted), it is meant that the substituent is substituted with one or more of the named R groups (e.g., $R^2$) as appropriate. In some embodiments, the substituent is substituted with only one of the named R groups.

Each R-group as provided in the formulae provided herein can appear more than once. Where an R-group appears more than once each R group can be optionally different.

The term "contacting" as used herein, refers to materials or compounds being sufficiently close in proximity to react or interact. For example, in methods of contacting an unrefined petroleum material, a hydrocarbon material bearing formation, and/or a well bore, the term "contacting" can include placing a compound (e.g., a surfactant) or an aqueous composition (e.g., chemical, surfactant or polymer) within a hydrocarbon material-bearing formation using any suitable manner known in the art (e.g., pumping, injecting, pouring, releasing, displacing, spotting or circulating the chemical into a well, well bore or hydrocarbon bearing formation).

The terms "unrefined petroleum" and "crude oil" are used interchangeably and in keeping with the plain ordinary usage of those terms. "Unrefined petroleum" and "crude oil" may be found in a variety of petroleum reservoirs (also referred to herein as a "reservoir," "oil field deposit" "deposit" and the like) and in a variety of forms including oleaginous materials, oil shales (i.e., organic-rich fine-grained sedimentary rock), tar sands, light oil deposits, heavy oil deposits, and the like. "Crude oils" or "unrefined petroleums" generally refer to a mixture of naturally occurring hydrocarbons that may be refined into diesel, gasoline, heating oil, jet fuel, kerosene, and other products called fuels or petrochemicals. Crude oils or unrefined petroleums are named according to their contents and origins, and are classified according to their per unit weight (specific gravity). Heavier crudes generally yield more heat upon burning, but have lower gravity as defined by the American Petroleum Institute (API) (i.e., API gravity) and market price in comparison to light (or sweet) crude oils. Crude oil may also be characterized by its Equivalent Alkane Carbon Number (EACN). The term "API gravity" refers to the measure of how heavy or light a petroleum liquid is compared to water.

If an oil's API gravity is greater than 10, it is lighter and floats on water, whereas if it is less than 10, it is heavier and sinks. API gravity is thus an inverse measure of the relative density of a petroleum liquid and the density of water. API gravity may also be used to compare the relative densities of petroleum liquids. For example, if one petroleum liquid floats on another and is therefore less dense, it has a greater API gravity.

Crude oils vary widely in appearance and viscosity from field to field. They range in color, odor, and in the properties they contain. While all crude oils are mostly hydrocarbons, the differences in properties, especially the variation in molecular structure, determine whether a crude oil is more or less easy to produce, pipeline, and refine. The variations may even influence its suitability for certain products and the quality of those products. Crude oils are roughly classified into three groups, according to the nature of the hydrocarbons they contain. (i) Paraffin-based crude oils contain higher molecular weight paraffins, which are solid at room temperature, but little or no asphaltic (bituminous) matter. They can produce high-grade lubricating oils. (ii) Asphaltene based crude oils contain large proportions of asphaltic matter, and little or no paraffin. Some are predominantly naphthenes and so yield lubricating oils that are sensitive to temperature changes than the paraffin-based crudes. (iii) Mixed based crude oils contain both paraffin and naphthenes, as well as aromatic hydrocarbons. Most crude oils fit this latter category.

"Reactive" crude oil, as referred to herein, is crude oil containing natural organic acidic components (also referred to herein as unrefined petroleum acid) or their precursors such as esters or lactones. These reactive crude oils can generate soaps (carboxylates) when reacted with alkali. More terms used interchangeably for crude oil throughout this disclosure are hydrocarbon material or active petroleum material. An "oil bank" or "oil cut" as referred to herein, is the crude oil that does not contain the injected chemicals and is pushed by the injected fluid during an enhanced oil recovery process. A "nonactive oil," as used herein, refers to an oil that is not substantially reactive or crude oil not containing significant amounts of natural organic acidic components or their precursors such as esters or lactones such that significant amounts of soaps are generated when reacted with alkali. A nonactive oil as referred to herein includes oils having an acid number of less than 0.5 mg KOH/g of oil.

"Unrefined petroleum acids" as referred to herein are carboxylic acids contained in active petroleum material (reactive crude oil). The unrefined petroleum acids contain $C_{11}$-$C_{20}$ alkyl chains, including napthenic acid mixtures. The recovery of such "reactive" oils may be performed using alkali (e.g., NaOH or $Na_2CO_3$) in a surfactant composition. The alkali reacts with the acid in the reactive oil to form soap in situ. These in situ generated soaps serve as a source of surfactants minimizing the levels of added surfactants, thus enabling efficient oil recovery from the reservoir.

The term "polymer" refers to a molecule having a structure that essentially includes the multiple repetitions of units derived, actually or conceptually, from molecules of low relative molecular mass. In some embodiments, the polymer is an oligomer.

The term "bonded" refers to having at least one of covalent bonding, hydrogen bonding, ionic bonding, Van Der Waals interactions, pi interactions, London forces or electrostatic interactions.

The term "productivity" as applied to a petroleum or oil well refers to the capacity of a well to produce hydrocarbons (e.g., unrefined petroleum); that is, the ratio of the hydrocarbon flow rate to the pressure drop, where the pressure drop is the difference between the average reservoir pressure and the flowing bottom hole well pressure (i.e., flow per unit of driving force).

The term "oil solubilization ratio" is defined as the volume of oil solubilized divided by the volume of surfactant in microemulsion. All the surfactant is presumed to be in the microemulsion phase. The oil solubilization ratio is applied for Winsor type I and type III behavior. The volume of oil solubilized is found by reading the change between initial aqueous level and excess oil (top) interface level. The oil solubilization ratio is calculated as follows:

$$\sigma_o = \frac{V_o}{V_s}$$

where $\sigma_o$ is the oil solubilization ratio, $V_o$ is the volume of oil solubilized, and $V_s$ is the volume of surfactant.

The term "water solubilization ratio" is defined as the volume of water solubilized divided by the volume of surfactant in microemulsion. All the surfactant is presumed to be in the microemulsion phase. The water solubilization ratio is applied for Winsor type III and type II behavior. The volume of water solubilized is found by reading the change between initial aqueous level and excess water (bottom) interface level. The water solubilization parameter is calculated as follows:

$$\sigma_w = \frac{V_w}{S_s}$$

where $\sigma_w$ is the water solubilization ratio, $V_w$ is the volume of oil solubilized, and $V_s$ is the volume of surfactant.

The optimum solubilization ratio occurs where the oil and water solubilization ratios are equal. The coarse nature of phase behavior screening often does not include a data point at optimum, so the solubilization ratio curves are drawn for the oil and water solubilization ratio data and the intersection of these two curves is defined as the optimum. The following is true for the optimum solubilization ratio:

$$\sigma_o = \sigma_w = \sigma^*$$

where $\sigma^*$ is the optimum solubilization ratio.

The term "solubility" or "solubilization" in general refers to the property of a solute, which can be a solid, liquid or gas, to dissolve in a solid, liquid or gaseous solvent thereby forming a homogenous solution of the solute in the solvent. Solubility occurs under dynamic equilibrium, which means that solubility results from the simultaneous and opposing processes of dissolution and phase joining (e.g., precipitation of solids). The solubility equilibrium occurs when the two processes proceed at a constant rate. The solubility of a given solute in a given solvent typically depends on temperature. For many solids dissolved in liquid water, the solubility increases with temperature. In liquid water at high temperatures, the solubility of ionic solutes tends to decrease due to the change of properties and structure of liquid water. In more particular, solubility and solubilization as referred to herein is the property of oil to dissolve in water and vice versa.

"Viscosity" refers to a fluid's internal resistance to flow or being deformed by shear or tensile stress. In other words, viscosity may be defined as thickness or internal friction of a liquid. Thus, water is "thin", having a lower viscosity, while oil is "thick", having a higher viscosity. More generally, the less viscous a fluid is, the greater its ease of fluidity.

The term "salinity" as used herein, refers to concentration of salt dissolved in an aqueous phases. Examples for such salts are without limitation, sodium chloride, magnesium and calcium sulfates, and bicarbonates. In more particular, the term salinity as it pertains to the present invention refers to the concentration of salts in brine and surfactant solutions.

The term "aqueous solution or aqueous formulation" refers to a solution in which the solvent is water. The term "emulsion, emulsion solution or emulsion formulation" refers to a mixture of two or more liquids which are normally immiscible. A non-limiting example for an emulsion is a mixture of oil and water.

The term "co-solvent," as used herein, refers to a compound having the ability to increase the solubility of a solute (e.g., a surfactant as disclosed herein) in the presence of an unrefined petroleum acid. In some embodiments, the co-solvents provided herein have a hydrophobic portion (alkyl or aryl chain), a hydrophilic portion (e.g., an alcohol) and optionally an alkoxy portion. Co-solvents as provided herein include alcohols (e.g., $C_1$-$C_6$ alcohols, $C_1$-$C_6$ diols), alkoxy alcohols (e.g., $C_1$-$C_6$ alkoxy alcohols, $C_1$-$C_6$ alkoxy diols, and phenyl alkoxy alcohols), glycol ether, glycol and glycerol. The term "alcohol" is used according to its ordinary meaning and refers to an organic compound containing an —OH groups attached to a carbon atom. The term "diol" is used according to its ordinary meaning and refers to an organic compound containing two —OH groups attached to two different carbon atoms. The term "alkoxy alcohol" is used according to its ordinary meaning and refers to an organic compound containing an alkoxy linker attached to a —OH group A "microemulsion" as referred to herein is a thermodynamically stable mixture of oil, water, and a stabilizing agents such as a surfactant or a co-solvent that may also include additional components such as alkali agents, polymers (e.g., water-soluble polymers) and a salt. In contrast, a "macroemulsion" as referred to herein is a thermodynamically unstable mixture of oil and water that may also include additional components. An "emulsion" as referred to herein may be a microemulsion or a macroemulsion.

Compounds

Provided herein are short hydrophobe anionic surfactants. The short hydrophobe anionic surfactants can be defined by Formula I below

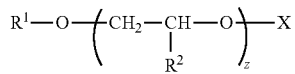

Formula I wherein $R^1$ is a $C_7$-$C_{12}$ alkyl group, an $R^3$-substituted aryl group, or an $R^3$-substituted cycloalkyl group; $R^2$ is independently hydrogen or methyl; $R^3$ is an alkyl group, wherein the alkyl group together with the aryl group or cycloalkyl group to which the alkyl group is attached comprise from 7 to 12 carbon atoms; z is an integer from 2 to 24 (e.g., an integer from 2 to 15); X is —$SO_3^-M^+$, —$SO_3^H$, —$CH_2C(O)O^-M^+$, —$CH_2C(O)OH$; and $M^+$ is a cation.

In some embodiments of Formula I, z can be at least 2 (e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23).

In some embodiments of Formula I, z can be 24 or less (e.g., 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, or 3 or less).

The integer z can range from any of the minimum values described above to any of the maximum values described above. For example, z can be an integer from 2 to 24 (e.g., an integer from 2 to 15, an integer from 3 to 15, an integer from 2 to 10, or an integer from 3 to 10).

In some cases, the short hydrophobe anionic surfactants can be defined by Formula II below

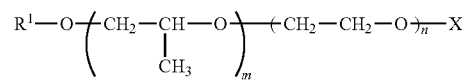

Formula II where $R^1$ is a $C_7$-$C_{12}$ alkyl group, an $R^3$-substituted aryl group, or an $R^3$-substituted cycloalkyl group; $R^3$ is an alkyl group, wherein the alkyl group together with the aryl group or cycloalkyl group to which the alkyl group is attached comprise from 7 to 12 carbon atoms; m is an integer from 2 to 24 and n is an integer from 0 to 22, with the proviso that the sum of m and n (m+n) is from 2 to 24; X is —$SO_3^-M^+$, —$SO_3^H$, —$CH_2C(O)O^-M^+$, —$CH_2C(O)OH$; and $M^+$ is a cation.

In some embodiments of Formula II, m can be at least 2 (e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23).

In some embodiments of Formula II, m can be 24 or less (e.g., 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, or 3 or less).

The integer m can range from any of the minimum values described above to any of the maximum values described above. For example, m can be an integer from 2 to 24 (e.g., an integer from 2 to 15, an integer from 3 to 15, an integer from 2 to 10, or an integer from 3 to 10).

In some embodiments of Formula II, n can be at least 0 (e.g., at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21).

In some embodiments of Formula II, m can be 22 or less (e.g., 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, 2 or less, or 1 or less).

The integer n can range from any of the minimum values described above to any of the maximum values described above. For example, n can be an integer from 0 to 22 (e.g., an integer from 0 to 15, an integer from 1 to 15, an integer from 0 to 10, or an integer from 1 to 10).

In embodiments of Formula II, the sum of m and n (m+n) can vary. For example, in some embodiments, the sum of m and n (m+n) can be at least 2 (e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23). In some embodiments of Formula II, the sum of m and n (m+n) can be 24 or less (e.g., 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, or 3 or less).

The sum of m and n (m+n) can range from any of the minimum values described above to any of the maximum values described above. For example, the sum of m and n (m+n) can range from 2 to 24 (e.g., from 2 to 15, from 3 to 15, from 2 to 10, or from 3 to 10).

In some embodiments of Formula II, m can be greater than n. In certain cases, m can be an integer from 3 to 10 and n can be an integer from 0 to 10, and the sum of m and n (m+n) can be from 3 to 15.

In some embodiments of Formula I and Formula II, $R^1$ can be a $C_7$-$C_{12}$ alkyl group. For example, $R^1$ can be a $C_7$ alkyl group, a $C_8$ alkyl group, a $C_9$ alkyl group, a $C_{10}$ alkyl group, a $C_{11}$ alkyl group, or a $C_{12}$ alkyl group. In some embodiments, $R^1$ can be a $C_7$-$C_{11}$ alkyl group. In some embodiments, $R^1$ can be a $C_7$-$C_{10}$ alkyl group. In some embodiments, $R^1$ can be a $C_7$-$C_9$ alkyl group. In some embodiments, $R^1$ can be a $C_7$-$C_8$ alkyl group. In some embodiments, $R^1$ can be a $C_8$-$C_{10}$ alkyl group. In some embodiments, $R^1$ can be a $C_9$-$C_{12}$ alkyl group. In some embodiments, $R^1$ can be a $C_{10}$-$C_{12}$ alkyl group. In some embodiments, $R^1$ can be a $C_{11}$-$C_{12}$ alkyl group. In some embodiments, $R^1$ can be a $C_8$-$C_{11}$ alkyl group. In some embodiments, $R^1$ can be a $C_8$-$C_{10}$ alkyl group. In some embodiments, $R^1$ can be a $C_8$-$C_9$ alkyl group. In some embodiments, $R^1$ can be a $C_9$-$C_{11}$ alkyl group. In some embodiments, $R^1$ can be a $C_9$-$C_{10}$ alkyl group. In some embodiments, $R^1$ can be a $C_{10}$-$C_{12}$ alkyl group. In some embodiments, $R^1$ can be a $C_{11}$-$C_{12}$ alkyl group. In each of these cases, the alkyl group can be branched or unbranched (i.e., linear). In each of these embodiments, the alkyl group can be saturated or unsaturated. In certain of these embodiments, the alkyl group can branched and saturated. For example, in certain embodiments of Formula I and Formula II, $R^1$ can be a branched, saturated $C_7$-$C_{12}$ alkyl group (e.g., a 2-ethylhexyl group).

In some embodiments of Formula I and Formula II, $R^1$ can be an $R^3$-substituted aryl group where $R^3$ is an alkyl group. The alkyl group together with the aryl group to which the alkyl group is attached can comprise 7 carbon atoms, 8 carbon atoms, 9 carbon atoms, 10 carbon atoms, 11 carbon atoms, or 12 carbon atoms. In some embodiments, the alkyl group together with the aryl group to which the alkyl group is attached can comprise at least 7 carbon atoms (e.g., at least 8 carbon atoms, at least 9 carbon atoms, at least 10 carbon atoms, or at least 11 carbon atoms). In some embodiments, the alkyl group together with the aryl group to which the alkyl group is attached can comprise 12 carbon atoms or less (e.g., 11 carbon atoms or less, 10 carbon atoms or less, 9 carbon atoms or less, or 8 carbon atoms or less). The alkyl group together with the aryl group to which the alkyl group is attached can comprise a number of carbon atoms ranging from any of the minimum values described above to any of the maximum values described above. For example, the alkyl group, together with the aryl group to which the alkyl group is attached, can comprise from 7 to 12 carbon atoms (e.g., from 7 to 11 carbon atoms, from 7 to 10 carbon atoms, from 7 to 9 carbon atoms, from 7 to 8 carbon atoms, from 8 to 12 carbon atoms, from 8 to 11 carbon atoms, from 8 to 10 carbon atoms, from 8 to 9 carbon atoms, from 9 to 12 carbon atoms, from 9 to 11 carbon atoms, from 9 to 10 carbon atoms, from 10 to 12 carbon atoms, from 10 to 11 carbon atoms, or from 11 to 12 carbon atoms).

By way of example, in some embodiments, the aryl group can comprise an $R^3$-substituted $C_6$ aryl group (e.g., a phenyl group), where $R^3$ is a $C_1$-$C_6$ alkyl group (e.g., a methyl, ethyl, n-propyl, isopropyl, n-butyl, t-butyl, isobutyl, or sec-butyl group, or n-pentyl, n-hexyl, or a homolog or isomer of n-pentyl or n-hexyl).

In some embodiments of Formula I and Formula II, $R^1$ can be an $R^3$-substituted cycloalkyl group where $R^3$ is an alkyl group. The alkyl group together with the cycloalkyl group to which the alkyl group is attached can comprise 7 carbon atoms, 8 carbon atoms, 9 carbon atoms, 10 carbon atoms, 11 carbon atoms, or 12 carbon atoms. In some embodiments, the alkyl group together with the cycloalkyl group to which the alkyl group is attached can comprise at least 7 carbon atoms (e.g., at least 8 carbon atoms, at least 9 carbon atoms, at least 10 carbon atoms, or at least 11 carbon atoms). In some embodiments, the alkyl group together with the cycloalkyl group to which the alkyl group is attached can comprise 12 carbon atoms or less (e.g., 11 carbon atoms or less, 10 carbon atoms or less, 9 carbon atoms or less, or 8 carbon atoms or less). The alkyl group together with the cycloalkyl group to which the alkyl group is attached can comprise a number of carbon atoms ranging from any of the minimum values described above to any of the maximum values described above. For example, the alkyl group, together with the cycloalkyl group to which the alkyl group is attached, can comprise from 7 to 12 carbon atoms (e.g., from 7 to 11 carbon atoms, from 7 to 10 carbon atoms, from 7 to 9 carbon atoms, from 7 to 8 carbon atoms, from 8 to 12 carbon atoms, from 8 to 11 carbon atoms, from 8 to 10 carbon atoms, from 8 to 9 carbon atoms, from 9 to 12 carbon atoms, from 9 to 11 carbon atoms, from 9 to 10 carbon atoms, from 10 to 12 carbon atoms, from 10 to 11 carbon atoms, or from 11 to 12 carbon atoms).

By way of example, in some embodiments, the cycloalkyl group can comprise an $R^3$-substituted $C_6$ cycloalkyl group (e.g., a cyclohexyl group), where $R^3$ is a $C_1$-$C_6$ alkyl group (e.g., a methyl, ethyl, n-propyl, isopropyl, n-butyl, t-butyl, isobutyl, or sec-butyl group, or n-pentyl, n-hexyl, or a homolog or isomer of n-pentyl or n-hexyl).

In some cases, the short hydrophobe anionic surfactant can be a sulfate surfactant. For example, in some embodiments of Formula I and Formula II, X can be —$SO_3^-M^+$ or —$SO_3H$. In some cases, the short hydrophobe anionic surfactant can be a carboxylate surfactant. For example, in some embodiments of Formula I and Formula II, X can be —$CH_2C(O)O^-M^-$ or —$CH_2C(O)OH$.

$M^+$ can be any appropriate counterion, such as a monovalent, divalent, or trivalent cation. In some embodiments, $M^+$ can be a monovalent or divalent cation (e.g., a metal cation). In some embodiments, $M^+$ can be a monovalent cation (e.g., a metal cation). In some embodiments, $M^+$ can be a divalent cation (e.g., a metal cation). Examples of suitable cations include, but are not limited to, $Na^+$, $K^+$, $NH_4^+$, $Ca^{2+}$, $Mg^{2+}$, and $Ba^{2+}$. A person having ordinary skill in the art will immediately recognize that $M^+$ may be a divalent cation where X is a monovalent anion (e.g., where $M^+$ is coordinated with more than one compound provided herein or with an additional anion in the surrounding liquid environment).

Aqueous Compositions

As described above, the short hydrophobe anionic surfactants described herein can be used in EOR formulations to impart many beneficial properties generally afforded by co-solvents. For example, the short hydrophobe anionic surfactants can provide for faster equilibration, low microemulsion viscosity, and improved aqueous stability. In particular, the short hydrophobe anionic surfactants described herein can impart one or more of these desirable properties (e.g., lower microemulsion viscosity) without increasing interfacial tension. Thus, the short hydrophobe anionic surfactants described herein can be incorporated into EOR formulations to increase aqueous stability, speed up equilibration, broaden the low interfacial tension region, decrease microemulsion viscosity, reduce surfactant retention, and combinations thereof. As the short hydrophobe anionic surfactants described herein can perform the dual role of surfactant and co-solvent in EOR formulations, the short hydrophobe anionic surfactants described herein can be used to prepare EOR formulations with lower amounts of co-solvent (or even EOR formulations that are free or substantially free from co-solvents). This improves the efficiency of the EOR process since co-solvents also partition into excess water and oil phases and whereas surfactants stay almost entirely in the membrane phase. The overall chemical cost of the EOR formulations may also be lowered.

Accordingly, also provided are aqueous compositions for use in EOR that comprise the short hydrophobe anionic surfactants described herein (e.g., a compound of Formula I or II). For example, provided herein are aqueous composition that comprise a short hydrophobe anionic surfactant described herein (e.g., a compound of Formula I or II) and an additional surfactant. As described herein, the additional surfactant is also referred to as a "co-surfactant."

The additional surfactant or co-surfactant, as used herein, is a compound within the aqueous composition that functions as a surface active agent when the aqueous composition is in contact with a crude oil (e.g., an unrefined petroleum). The co-surfactant, along with the compound of Formula I or II, may act to lower the interfacial tension and/or surface tension of the unrefined petroleum. In some embodiments, the co-surfactant and the compound of Formula I or II are present in synergistic surface active amounts. A "synergistic surface active amount," as used herein, means that a compound of Formula I or II and the co-surfactant are present in amounts in which the oil surface activity (interfacial tension lowering effect and/or surface tension lowering effect on crude oil when the aqueous composition is added to the crude oil) of the compound and co-surfactant combined is greater than the additive oil surface activity of the co-surfactant individually and the compound individually. In some cases, the oil surface activity of the compound and co-surfactant combination is 10%, 20%, 30%, 40%, 50%, 60%, 70%, 80%, 90% or 100% more than the additive oil surface activity of the co-surfactant individually and the compound individually. In some embodiments, the oil surface activity of the compound and co-surfactant combination is 2, 3, 4, 5, 6, 7, 8, 9 or 10 times more than the additive oil surface activity of the co-surfactant individually and the compound individually.

In another embodiment, the compound and co-surfactant are present in a surfactant stabilizing amount. A "surfactant stabilizing amount" means that the compound and the co-surfactant are present in an amount in which the co-surfactant degrades at a slower rate in the presence of the compound than in the absence of the compound, and/or the compound degrades at a slower rate in the presence of the co-surfactant than in the absence of the co-surfactant. The rate of degradation may be 10%, 20%, 30%, 40%, 50%, 60%, 70%, 80%, 90% or 100% slower. In some embodiments, the rate of degradation is 2, 3, 4, 5, 6, 7, 8, 9 or 10 times slower.

In another embodiment, the compound and co-surfactant are present in a synergistic solubilizing amount. A "synergistic solubilizing amount" means that the compound and the co-surfactant are present in an amount in which the compound is more soluble in the presence of the co-surfactant than in the absence of the surfactant, and/or the co-surfactant is more soluble in the presence of the compound than in the absence of the compound. The solubilization may be 10%, 20%, 30%, 40%, 50%, 60%, 70%, 80%, 90% or 100% higher. In some embodiment, the solubilization is 2, 3, 4, 5, 6, 7, 8, 9 or 10 times higher. In some embodiments, the compound is present in an amount sufficient to increase the solubility of the co-surfactant in the aqueous composition relative to the absence of the compound. In other words, in the presence of a sufficient amount of the compound, the solubility of the co-surfactant in the aqueous composition is higher than in the absence of the compound. In other embodiments, the co-surfactant is present in an amount sufficient to increase the solubility of the compound in the aqueous composition relative to the absence of the co-surfactant. Thus, in the presence of a sufficient amount of the co-surfactant the solubility of the compound in the aqueous solution is higher than in the absence of the co-surfactant.

In some embodiments, a single type of co-surfactant is in the aqueous composition. In other embodiments, a co-surfactant can comprise a blend of surfactants (e.g., a combination of two or more surfactants). The co-surfactant blend can comprise a mixture of a plurality of co-surfactant types. For example, the co-surfactant blend can include at least two co-surfactant types, at least three co-surfactant types, at least four co-surfactant types, at least five co-surfactant types, at least six co-surfactant types, or more. In some embodiments, the co-surfactant blend can include from two to six co-surfactant types (e.g., from two to five co-surfactant types, from two to four co-surfactant types, from two to three co-surfactant types, from three to six co-surfactant types, or from three to five co-surfactant types). The co-surfactant types can be independently different (e.g., anionic or cationic co-surfactants; two anionic co-surfactants having a different hydrocarbon chain length but are otherwise the same; a sulfate and a sulfonate surfactant that that the same hydrocarbon chain length and are otherwise the same, etc.). Therefore, a person having ordinary skill in the art will immediately recognize that the terms "co-surfactant" and "co-surfactant type(s)" have the same meaning and can be used interchangeably.

In some embodiments, the co-surfactant can comprise an anionic surfactant, a non-ionic surfactant, a zwitterionic surfactant, a cationic surfactant, or a combination thereof. In some embodiments, the co-surfactant can comprise an anionic surfactant, a non-ionic surfactant, or a combination thereof. In some embodiments, the co-surfactant can comprise a plurality of anionic surfactants. In some embodiments, the co-surfactant can comprise a zwitterionic co-surfactant. "Zwitterionic" or "zwitterion" as used herein refers to a neutral molecule with a positive (or cationic) and a negative (or anionic) electrical charge at different locations within the same molecule. Examples of zwitterionic surfactants include without limitation betains and sultains.

The co-surfactant can be any appropriate co-surfactant useful in the field of enhanced oil recovery. For example, in some embodiments, the co-surfactant can comprise an internal olefin sulfonate (IOS), an alpha olefin sulfonate (AOS), an alkyl aryl sulfonate (ARS), an alkane sulfonate, a petroleum sulfonate, an alkyl diphenyl oxide (di)sulfonate, an alcohol sulfate, an alkoxy sulfate, an alkoxy sulfonate, an alcohol phosphate, an alkoxy phosphate, a sulfosuccinate ester, an alcohol ethoxylate, an alkyl phenol ethoxylate, a quaternary ammonium salt, a betaine or sultaine. The co-surfactant as provided herein, can also be a soap.

In embodiments, the co-surfactant can comprise an anionic surfactant. For example, the co-surfactant can comprise an anionic surfactant selected from the group consisting of alkoxy carboxylate surfactants, alkoxy sulfate surfactants, alkoxy sulfonate surfactants, alkyl sulfonate surfactants, aryl sulfonate surfactants, olefin sulfonate surfactants, and combinations thereof. In embodiments, the anionic surfactant can comprise an anionic surfactant blend. Where the anionic surfactant is an anionic surfactant blend, the aqueous composition includes a plurality (i.e., more than one) type of anionic surfactant.

In some embodiments, the co-surfactant can comprise an alkoxy carboxylate surfactant. An "alkoxy carboxylate surfactant" as provided herein is a compound having an alkyl or aryl attached to one or more alkoxylene groups (typically —$CH_2$—$CH$(ethyl)-$O$—, —$CH_2$—$CH$(methyl)-$O$—, or —$CH_2$—$CH_2$—$O$—) which, in turn is attached to —$COO^-$ or acid or salt thereof including metal cations such as sodium. In some embodiments, the co-surfactant can comprise an alkoxy carboxylate surfactant defined by Formula III or Formula IV

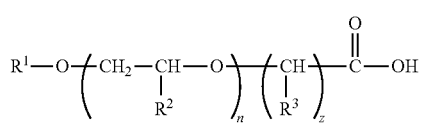

Formula III

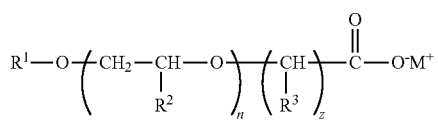

Formula IV wherein $R^1$ is substituted or unsubstituted $C_8$-$C_{150}$ alkyl or substituted or unsubstituted aryl; $R^2$ is independently hydrogen or unsubstituted $C_1$-$C_6$ alkyl; $R^3$ is independently hydrogen or unsubstituted $C_1$-$C_6$ alkyl; n is an integer from 2 to 210; z is an integer from 1 to 6; and $M^+$ is a cation.

In embodiments of Formula III or IV, $R^1$ is unsubstituted linear or branched $C_8$-$C_{36}$ alkyl. In embodiments of Formula III or IV, $R^1$ is ($C_6H_5$—$CH_2CH_2$)$_3$$C_6H_2$— (TSP), ($C_6H_5$—$CH_2CH_2$)$_2$$C_6H_3$— (DSP), ($C_6H_5$—$CH_2CH_2$)$_1$$C_6H_4$— (MSP), or substituted or unsubstituted naphthyl. In embodiments of Formula III or IV, the alkoxy carboxylate is $C_{28}$-25PO-25EO-carboxylate (i.e., unsubstituted $C_{28}$ alkyl attached to 25 —$CH_2$—$CH$(methyl)-$O$-linkers, attached in turn to 25 —$CH_2$—$CH_2$—$O$— linkers, attached in turn to —$COO^-$ or acid or salt thereof including metal cations such as sodium).

In some embodiments, the co-surfactant can comprise an alkoxy sulfate surfactant. An alkoxy sulfate surfactant as provided herein is a surfactant having an alkyl or aryl attached to one or more alkoxylene groups (typically —$CH_2$—$CH$(ethyl)-$O$—, —$CH_2$—$CH$(methyl)-$O$—, or —$CH_2$—$CH_2$—$O$—) which, in turn is attached to —$SO_3^-$ or acid or salt thereof including metal cations such as sodium. In embodiments, the alkoxy sulfate surfactant can be defined by the formula below

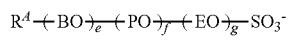

or acid or salt thereof, wherein $R^A$ is $C_8$-$C_{36}$ alkyl group; BO represents —$CH_2$—$CH$(ethyl)-$O$—; PO represents —$CH_2$—$CH$(methyl)-$O$—; EO represents —$CH_2$—$CH_2$—$O$—; and e, f and g are each independently integers from 0 to 50, with the proviso that at least one of e, f, and g is not zero. In embodiments, the alkoxy sulfate surfactant can be $C_{15}$-13PO-sulfate (i.e., an unsubstituted $C_{15}$ alkyl attached to 13 —$CH_2$—$CH$(methyl)-$O$— linkers, in turn attached to —$SO_3^-$ or acid or salt thereof including metal cations such as sodium). In embodiments, the alkoxy sulfate surfactant can be $C_{13}$-13PO-sulfate (i.e., an unsubstituted $C_{13}$ alkyl attached to 13 —$CH_2$—$CH$(methyl)-$O$— linkers, in turn attached to —$SO_3^-$ or acid or salt thereof including metal cations such as sodium).

In some embodiments, the co-surfactant can comprise an alkoxy sulfate surfactant defined by Formula V

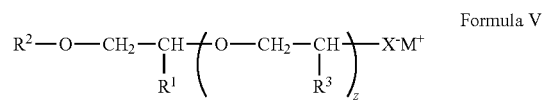

Formula V wherein $R^1$ and $R^2$ are independently a substituted or unsubstituted $C_8$-$C_{150}$ alkyl group or a substituted or unsubstituted aryl group; $R^3$ is independently hydrogen or unsubstituted $C_1$-$C_6$ alkyl; z is an integer from 2 to 210; $X^-$ is

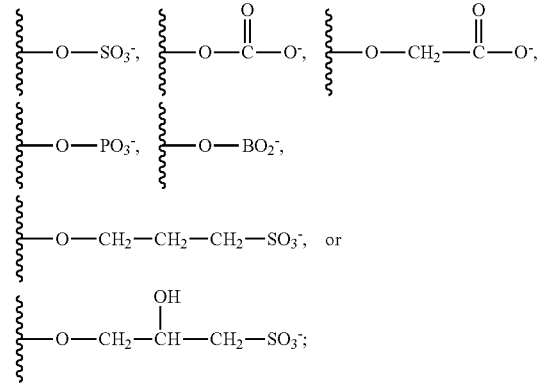

and $M^+$ is a cation.

In some embodiments of Formula V, $R^1$ is a branched unsubstituted $C_8$-$C_{150}$ group. In embodiments of Formula V, $R^1$ is branched or linear unsubstituted $C_{12}$-$C_{100}$ alkyl, ($C_6H_5$—$CH_2CH_2$)$_3$$C_6H_2$— (TSP), ($C_6H_5$—$CH_2CH_2$)$_2$$C_6H_3$— (DSP), ($C_6H_5$—$CH_2CH_2$)$_1$$C_6H_4$— (MSP), or substituted or unsubstituted naphthyl. In embodiments of Formula V, the alkoxy sulfate is $C_{16}$-$C_{16}$-epoxide-15PO-10EO-sulfate (i.e., a linear unsubstituted $C_{16}$ alkyl attached to an oxygen, which in turn is attached to a branched unsubstituted $C_{16}$ alkyl, which in turn is attached to 15 —$CH_2$—$CH$(methyl)-$O$— linkers, in turn attached to 10 —$CH_2$—$CH_2$—$O$— linkers, in turn attached to —$SO_3^-$ or acid or salt thereof including metal cations such as sodium).

In some embodiments, the alkoxy sulfate surfactant provided herein can be an aryl alkoxy sulfate surfactant. An aryl alkoxy surfactant as provided herein is an alkoxy surfactant having an aryl attached to one or more alkoxylene groups (typically —$CH_2$—$CH$(ethyl)-$O$—, —$CH_2$—$CH$(methyl)-$O$—, or —$CH_2$—$CH_2$—$O$—) which, in turn is attached to —$SO_3^-$ or acid or salt thereof including metal cations such as sodium. In embodiments of Formula V, the aryl alkoxy sulfate surfactant is $(C_6H_5-CH_2CH_2)_3C_6H_2$-7PO-10EO-sulfate (i.e., tri-styrylphenol attached to 7 —$CH_2$—CH(methyl)-O— linkers, in turn attached to 10 —$CH_2$—$CH_2$—O— linkers, in turn attached to —$SO_3^-$ or acid or salt thereof including metal cations such as sodium).

In some embodiments, the co-surfactant can comprise an unsubstituted alkyl sulfate and/or an unsubstituted alkyl sulfonate surfactant. An alkyl sulfate surfactant as provided herein is a surfactant having an alkyl group attached to —O—$SO_3^-$ or acid or salt thereof including metal cations such as sodium. An alkyl sulfonate surfactant as provided herein is a surfactant having an alkyl group attached to —$SO_3^-$ or acid or salt thereof including metal cations such as sodium. In some embodiments, the co-surfactant can comprise an unsubstituted aryl sulfate surfactant or an unsubstituted aryl sulfonate surfactant. An aryl sulfate surfactant as provided herein is a surfactant having an aryl group attached to —O—$SO_3^-$ or acid or salt thereof including metal cations such as sodium. An aryl sulfonate surfactant as provided herein is a surfactant having an aryl group attached to —$SO_3^-$ or acid or salt thereof including metal cations such as sodium. In some embodiments, the co-surfactant can comprise an alkyl aryl sulfonate. Non-limiting examples of alkyl sulfate surfactants, aryl sulfate surfactants, alkyl sulfonate surfactants, aryl sulfonate surfactants and alkyl aryl sulfonate surfactants useful in the embodiments provided herein are alkyl aryl sulfonates (ARS) (e.g., alkyl benzene sulfonate (ABS) such as a $C_8$-$C_{30}$ ABS), alkane sulfonates, petroleum sulfonates, and alkyl diphenyl oxide (di)sulfonates. Additional surfactants useful in the embodiments provided herein are alcohol sulfates, alcohol phosphates, alkoxy phosphate, sulfosuccinate esters, alcohol ethoxylates, alkyl phenol ethoxylates, quaternary ammonium salts, betains and sultains.

In some embodiments, the co-surfactant can comprise an olefin sulfonate surfactant. In embodiments, the olefin sulfonate surfactant can be an internal olefin sulfonate (IOS) or an alpha olefin sulfonate (AOS). In embodiments, the olefin sulfonate surfactant can be a $C_{10}$-$C_{30}$ (IOS). In embodiments, the olefin sulfonate surfactant is $C_{15}$-$C_{18}$ IOS. In embodiments, the olefin sulfonate surfactant is $C_{19}$-$C_{28}$ IOS. Where the olefin sulfonate surfactant is $C_{15}$-$C_{18}$ IOS, the olefin sulfonate surfactant can be a mixture (combination) of $C_{15}$, $C_{16}$, $C_{17}$ and $C_{18}$ alkene, wherein each alkene is attached to a —$SO_3^-$ or acid or salt thereof including metal cations such as sodium. Likewise, where the olefin sulfonate surfactant is $C_{19}$-$C_{28}$ IOS, the olefin sulfonate surfactant can be a mixture (combination) of $C_{19}$, $C_{20}$, $C_{21}$, $C_{22}$, $C_{23}$, $C_{24}$, $C_{25}$, $C_{26}$, $C_{27}$ and $C_{28}$ alkene, wherein each alkene is attached to a —$SO_3^-$ or acid or salt thereof including metal cations such as sodium. In embodiments, the olefin sulfonate surfactant is $C_{19}$-$C_{23}$ IOS. As mentioned above, the aqueous composition provided herein may include a plurality of co-surfactants (i.e., a co-surfactant blend). In some embodiments, the co-surfactant blend can comprise a first olefin sulfonate surfactant and a second olefin sulfonate surfactant. In embodiments, the first olefin sulfonate surfactant can be a $C_{15}$-$C_{18}$ IOS and the second olefin sulfonate surfactant can be a $C_{19}$-$C_{28}$ IOS.

In some embodiments, the co-surfactant can comprise a surfactant defined by Formula VI

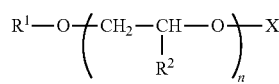

Formula VI wherein $R^1$ is an $R^4$-substituted or unsubstituted $C_8$-$C_{20}$ alkyl group, an $R^3$-substituted or unsubstituted aryl group, or an $R^3$-substituted or unsubstituted cycloalkyl group; $R^2$ is independently hydrogen or methyl; $R^3$ is independently an $R^4$-substituted or unsubstituted $C_1$-$C_{15}$ alkyl group, an $R^4$-substituted or unsubstituted aryl group, or an $R^4$-substituted or unsubstituted cycloalkyl group; $R^4$ is independently an unsubstituted aryl group or an unsubstituted cycloalkyl group; n is an integer from 25 to 115; X is X is —$SO_3^-M^+$, —$SO_3^H$, —$CH_2C(O)O^-M^+$, —$CH_2C(O)OH$; and $M^+$ is a cation.

In some embodiments of Formula VI, the symbol n is an integer from 25 to 115. In some embodiments of Formula VI, the symbol n is an integer from 30 to 115. In some embodiments of Formula VI, the symbol n is an integer from 35 to 115. In some embodiments of Formula VI, the symbol n is an integer from 40 to 115. In some embodiments of Formula VI, the symbol n is an integer from 45 to 115. In some embodiments of Formula VI, the symbol n is an integer from 50 to 115. In some embodiments of Formula VI, the symbol n is an integer from 55 to 115. In some embodiments of Formula VI, the symbol n is an integer from 60 to 115. In some embodiments of Formula VI, the symbol n is an integer from 65 to 115. In some embodiments of Formula VI, the symbol n is an integer from 70 to 115. In some embodiments of Formula VI, the symbol n is an integer from 75 to 115. In some embodiments of Formula VI, the symbol n is an integer from 80 to 115. In some embodiments of Formula VI, the symbol n is an integer from 30 to 80. In some embodiments of Formula VI, the symbol n is an integer from 35 to 80. In some embodiments of Formula VI, the symbol n is an integer from 40 to 80. In some embodiments of Formula VI, the symbol n is an integer from 45 to 80. In some embodiments of Formula VI, the symbol n is an integer from 50 to 80. In some embodiments of Formula VI, the symbol n is an integer from 55 to 80. In some embodiments of Formula VI, the symbol n is an integer from 60 to 80. In some embodiments of Formula VI, the symbol n is an integer from 65 to 80. In some embodiments of Formula VI, the symbol n is an integer from 70 to 80. In some embodiments of Formula VI, the symbol n is an integer from 75 to 80. In some embodiments of Formula VI, the symbol n is an integer from 30 to 60. In some embodiments of Formula VI, the symbol n is an integer from 35 to 60. In some embodiments of Formula VI, the symbol n is an integer from 40 to 60. In some embodiments of Formula VI, the symbol n is an integer from 45 to 60. In some embodiments of Formula VI, the symbol n is an integer from 50 to 60. In some embodiments of Formula VI, the symbol n is an integer from 55 to 60. In embodiments of Formula VI, n is 25. In embodiments of Formula VI, n is 50. In embodiments of Formula VI, n is 55. In embodiments of Formula VI, n is 75.

In some embodiments of Formula VI, $R^1$ is $R^4$-substituted or unsubstituted $C_8$-$C_{20}$ alkyl. In embodiments of Formula VI, $R^1$ is $R^4$-substituted or unsubstituted $C_{12}$-$C_{20}$ alkyl. In embodiments of Formula VI, $R^1$ is $R^4$-substituted or unsubstituted $C_{13}$-$C_{20}$ alkyl. In embodiments of Formula VI, $R^1$ is $R^4$-substituted or unsubstituted $C_{13}$ alkyl. In embodiments of Formula VI, $R^1$ is unsubstituted $C_{13}$ alkyl. In other related embodiments, $R^1$ is a unsubstituted tridecyl (i.e., a $C_{13}H_{27}$-alkyl radical derived from tridecylalcohol). In yet embodiments, $R^1$ is $R^4$-substituted or unsubstituted $C_{15}$-$C_{20}$ alkyl. In embodiments of Formula VI, $R^1$ is $R^4$-substituted or unsubstituted $C_{18}$ alkyl. In embodiments of Formula VI, $R^1$ is unsubstituted $C_{18}$ alkyl. In other related embodiments, $R^1$ is an unsubstituted oleyl (i.e., a $C_{17}H_{33}CH_2$— radical derived from oleyl alcohol).

In some embodiments of Formula VI, $R^1$ can be $R^4$-substituted or unsubstituted alkyl. In embodiments of Formula VI, $R^1$ is $R^4$-substituted or unsubstituted $C_8$-$C_{20}$ alkyl. In embodiments of Formula VI, $R^1$ is $R^4$-substituted or unsubstituted $C_{10}$-$C_{20}$ alkyl. In embodiments of Formula VI, $R^1$ is $R^4$-substituted or unsubstituted $C_{12}$-$C_{20}$ alkyl. In embodiments of Formula VI, $R^1$ is $R^4$-substituted or unsubstituted $C_{13}$-$C_{20}$ alkyl. In embodiments of Formula VI, $R^1$ is $R^4$-substituted or unsubstituted $C_{14}$-$C_{20}$ alkyl. In embodiments of Formula VI, $R^1$ is $R^4$-substituted or unsubstituted $C_{16}$-$C_{20}$ alkyl. In embodiments of Formula VI, $R^1$ is $R^4$-substituted or unsubstituted $C_8$-$C_{15}$ alkyl. In embodiments of Formula VI, $R^1$ is $R^4$-substituted or unsubstituted $C_{10}$-$C_{15}$ alkyl. In embodiments of Formula VI, $R^1$ is $R^4$-substituted or unsubstituted $C_{12}$-$C_{15}$ alkyl. In embodiments of Formula VI, $R^1$ is $R^4$-substituted or unsubstituted $C_{13}$-$C_{15}$ alkyl. In related embodiments, the alkyl is a saturated alkyl. In other related embodiments, $R^1$ is $R^4$-substituted or unsubstituted $C_{13}$ alkyl. In other related embodiments, $R^1$ is unsubstituted $C_{13}$ alkyl. In other related embodiments, $R^1$ is a tridecyl (i.e., a $C_{13}H_{27}$-alkyl radical derived from tridecylalcohol). In other related embodiments, $R^1$ is $R^4$-substituted or unsubstituted $C_{18}$ alkyl. In other related embodiments, $R^1$ is unsubstituted $C_{18}$ alkyl. In other related embodiments, $R^1$ is an oleyl (i.e., a $C_{17}H_{33}CH_2$— radical derived from oleyl alcohol). In other related embodiments, n is as defined in an embodiment above (e.g., n is at least 40, or at least 50, e.g., 55 to 85).

In some embodiments of Formula VI, $R^1$ can be a linear or branched unsubstituted $C_8$-$C_{20}$ alkyl group. In embodiments of Formula VI, $R^1$ is branched unsubstituted $C_8$-$C_{20}$ alkyl. In embodiments of Formula VI, $R^1$ is linear unsubstituted $C_8$-$C_{20}$ alkyl. In embodiments of Formula VI, $R^1$ is branched unsubstituted $C_8$-$C_{18}$ alkyl. In embodiments of Formula VI, $R^1$ is branched unsubstituted $C_8$-$C_{18}$ alkyl. In embodiments of Formula VI, $R^1$ is linear unsubstituted $C_8$-$C_{18}$ alkyl. In embodiments of Formula VI, $R^1$ is branched unsubstituted $C_{18}$ alkyl. In other related embodiments, $R^1$ is an oleyl (i.e., a $C_{17}H_{33}CH_2$— radical derived from oleyl alcohol). In embodiments of Formula VI, $R^1$ is linear or branched unsubstituted $C_8$-$C_{16}$ alkyl. In embodiments of Formula VI, $R^1$ is branched unsubstituted $C_8$-$C_{16}$ alkyl. In embodiments of Formula VI, $R^1$ is linear unsubstituted $C_8$-$C_{16}$ alkyl. In embodiments of Formula VI, $R^1$ is linear or branched unsubstituted $C_8$-$C_{14}$ alkyl. In embodiments of Formula VI, $R^1$ is branched unsubstituted $C_8$-$C_{14}$ alkyl. In embodiments of Formula VI, $R^1$ is linear unsubstituted $C_8$-$C_{14}$ alkyl. In other related embodiments, $R^1$ is branched unsubstituted $C_{13}$ alkyl. In other related embodiments, $R^1$ is a tridecyl (i.e., a $C_{13}H_{27}$— alkyl radical derived from tridecylalcohol). In embodiments of Formula VI, $R^1$ is linear or branched unsubstituted $C_8$-$C_{12}$ alkyl. In embodiments of Formula VI, $R^1$ is branched unsubstituted $C_8$-$C_{12}$ alkyl. In embodiments of Formula VI, $R^1$ is linear unsubstituted $C_8$-$C_{12}$ alkyl. In other related embodiments, n is as defined in an embodiment above (e.g., n is at least 40, or at least 50, e.g., 55 to 85).

In some embodiments of Formula VI where $R^1$ is a linear or branched unsubstituted alkyl (e.g., branched unsubstituted $C_{10}$-$C_{20}$ alkyl), the alkyl can be a saturated alkyl (e.g., a linear or branched unsubstituted saturated alkyl or branched unsubstituted $C_{10}$-$C_{20}$ saturated alkyl). A "saturated alkyl," as used herein, refers to an alkyl consisting only of hydrogen and carbon atoms that are bonded exclusively by single bonds. Thus, in embodiments of Formula VI, $R^1$ may be linear or branched unsubstituted saturated alkyl. In embodiments of Formula VI, $R^1$ is branched unsubstituted $C_{10}$-$C_{20}$ saturated alkyl. In embodiments of Formula VI, $R^1$ is linear unsubstituted $C_{10}$-$C_{20}$ saturated alkyl. In embodiments of Formula VI, $R^1$ is branched unsubstituted $C_{12}$-$C_{20}$ saturated alkyl. In embodiments of Formula VI, $R^1$ is linear unsubstituted $C_{12}$-$C_{20}$ saturated alkyl. In embodiments of Formula VI, $R^1$ is branched unsubstituted $C_{12}$-$C_{16}$ saturated alkyl. In embodiments of Formula VI, $R^1$ is linear unsubstituted $C_{12}$-$C_{16}$ saturated alkyl. In some further embodiments, $R^1$ is linear unsubstituted $C_{13}$ saturated alkyl.

In some embodiments of Formula VI where $R^1$ is a linear or branched unsubstituted alkyl (e.g., branched unsubstituted $C_{10}$-$C_{20}$ alkyl), the alkyl can be an unsaturated alkyl (e.g., a linear or branched unsubstituted unsaturated alkyl or branched unsubstituted $C_{10}$-$C_{20}$ unsaturated alkyl). An "unsaturated alkyl," as used herein, refers to an alkyl having one or more double bonds or triple bonds. An unsaturated alkyl as provided herein can be mono- or polyunsaturated and can include di- and multivalent radicals. Thus, in embodiments of Formula VI, $R^1$ may be linear or branched unsubstituted unsaturated alkyl. In embodiments of Formula VI, $R^1$ is branched unsubstituted $C_{10}$-$C_{20}$ unsaturated alkyl. In embodiments of Formula VI, $R^1$ is linear unsubstituted $C_{10}$-$C_{20}$ unsaturated alkyl. In embodiments of Formula VI, $R^1$ is branched unsubstituted $C_{12}$-$C_{20}$ unsaturated alkyl. In embodiments of Formula VI, $R^1$ is linear unsubstituted $C_{12}$-$C_{20}$ unsaturated alkyl. In embodiments of Formula VI, $R^1$ is branched unsubstituted $C_{12}$-$C_{18}$ unsaturated alkyl. In embodiments of Formula VI, $R^1$ is linear unsubstituted $C_{12}$-$C_{18}$ unsaturated alkyl. In embodiments of Formula VI, $R^1$ is linear unsubstituted $C_{18}$ unsaturated alkyl. In embodiments of Formula VI, $R^1$ is branched unsubstituted $C_{18}$ unsaturated alkyl. In one embodiment, $R^1$ is linear unsubstituted $C_{18}$ mono-unsaturated alkyl. In another embodiment, $R^1$ is linear unsubstituted $C_{18}$ poly-unsaturated alkyl. In one embodiment, $R^1$ is branched unsubstituted $C_{18}$ mono-unsaturated alkyl. In another embodiment, $R^1$ is branched unsubstituted $C_{18}$ poly-unsaturated alkyl.

In some embodiments of Formula VI, $R^1$ can be $R^4$-substituted or unsubstituted $C_8$-$C_{20}$ (e.g., $C_{12}$-$C_{18}$) alkyl, $R^3$-substituted or unsubstituted $C_5$-$C_{10}$ (e.g., $C_5$-$C_6$) aryl or $R^3$-substituted or unsubstituted $C_3$-$C_8$ (e.g., $C_5$-$C_7$) cycloalkyl. $R^3$ can be independently $R^4$-substituted or unsubstituted $C_1$-$C_{15}$ (e.g., $C_8$-$C_{12}$) alkyl, $R^4$-substituted or unsubstituted $C_5$-$C_{10}$ (e.g., $C_5$-$C_6$) aryl or $R^4$-substituted or unsubstituted $C_3$-$C_8$ (e.g., $C_5$-$C_7$) cycloalkyl. Thus, in embodiments of Formula VI, $R^3$ is $R^4$-substituted or unsubstituted $C_1$-$C_{15}$ alkyl, $R^4$-substituted or unsubstituted $C_5$-$C_{10}$ aryl or $R^4$-substituted or unsubstituted $C_3$-$C_8$ cycloalkyl. $R^4$ can be independently unsubstituted $C_5$-$C_{10}$ (e.g., $C_5$-$C_6$) aryl or unsubstituted $C_3$-$C_8$ (e.g., $C_5$-$C_7$) cycloalkyl. Thus, in embodiments of Formula VI, $R^4$ is independently unsubstituted $C_5$-$C_{10}$ aryl or unsubstituted $C_3$-$C_8$ cycloalkyl.

In some embodiments, the co-surfactant can comprise a surfactant defined by Formula VII Formula VII

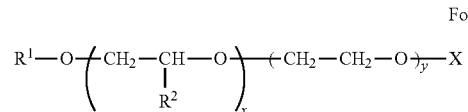

wherein $R^1$ and X are defined as above (e.g., in Formula VI); y is an integer from 5 to 40; and x is an integer from 35 to 50.

In embodiments of Formula VII, y is 10 and x is 45. In embodiments of Formula VII, $R^1$ is $C_{13}$ alkyl. In embodiments of Formula VII, y is 30 and x is 45. In some other embodiments, $R^1$ is unsubstituted unsaturated $C_{18}$ alkyl. In embodiments of Formula VII, $R^1$ is linear unsubstituted $C_{18}$ unsaturated alkyl. In embodiments of Formula VII, $R^1$ is branched unsubstituted $C_{18}$ unsaturated alkyl. In one embodiment, $R^1$ is linear unsubstituted $C_{18}$ mono-unsaturated alkyl. In another embodiment, $R^1$ is linear unsubstituted $C_{18}$ poly-unsaturated alkyl. In one embodiment, $R^1$ is branched unsubstituted $C_{18}$ mono-unsaturated alkyl. In another embodiment, $R^1$ is branched unsubstituted $C_{18}$ poly-unsaturated alkyl.

In some embodiments of Formula VII where $R^1$ is unsubstituted $C_{13}$ alkyl, n is 55, X is $-SO_3^-M^+$, and $M^+$ is a divalent cation (e.g., $Na^{2+}$). In embodiments of Formula VII, x is 45 and y Is 10. In some embodiments of the compound of Formula VII where $R^1$ is unsubstituted $C_{18}$ unsaturated alkyl, n is 75, X is $-CH_2C(O)O^-M^+$, and $M^+$ is a monovalent cation (e.g., $Na^+$). In embodiments of Formula VII, x is 45 and y is 30.

Suitable co-surfactants are disclosed, for example, in U.S. Pat. Nos. 3,811,504, 3,811,505, 3,811,507, 3,890,239, 4,463,806, 6,022,843, 6,225,267, and 7,629,299; International Patent Application Publication Nos. WO/2008/079855, WO/2012/027757 and WO/2011/094442; as well as U.S. Patent Application Publication Nos. 2005/0199395, 2006/0185845, 2006/018486, 2009/0270281, 2011/0046024, 2011/0100402, 2011/0190175, 2007/191633, 2010/004843, 2011/0201531, 2011/0190174, 2011/0071057, 2011/0059873, 2011/0059872, 2011/0048721, 2010/0319920, 2010/0292110, and 2013/0281327, all of which are incorporated herein by reference in their entirety. Additional suitable co-surfactants are surfactants known to be used in enhanced oil recovery methods, including those discussed in D. B. Levitt, A. C. Jackson, L. Britton and G. A. Pope, "Identification and Evaluation of High-Performance EOR Surfactants," SPE IX89, conference contribution for the SPE Symposium on Improved Oil Recovery Annual Meeting, Tulsa, Okla., Apr. 24-26, 2006.

A person having ordinary skill in the art will immediately recognize that many surfactants are commercially available as blends of related molecules (e.g., IOS and ABS surfactants). Thus, where a surfactant is present within a composition provided herein, a person of ordinary skill would understand that the surfactant might be a blend of a plurality of related surfactant molecules (as described herein and as generally known in the art).

In some embodiments, the total surfactant concentration (i.e., the compound of Formula I or II and one or more co-surfactants within the aqueous compositions provided herein) is from about 0.05% w/w to about 10% w/w. In other embodiments, the total surfactant concentration in the aqueous composition is from about 0.25% w/w to about 10% w/w. In other embodiments, the total surfactant concentration in the aqueous composition is about 0.5% w/w. In other embodiments, the total surfactant concentration in the aqueous composition is about 1.0% w/w. In other embodiments, the total surfactant concentration in the aqueous composition is about 1.25% w/w. In other embodiments, the total surfactant concentration in the aqueous composition is about 1.5% w/w. In other embodiments, the total surfactant concentration in the aqueous composition is about 1.75% w/w. In other embodiments, the total surfactant concentration in the aqueous composition is about 2.0% w/w. In other embodiments, the total surfactant concentration in the aqueous composition is about 2.5% w/w. In other embodiments, the total surfactant concentration in the aqueous composition is about 3.0% w/w. In other embodiments, the total surfactant concentration in the aqueous composition is about 3.5% w/w. In other embodiments, the total surfactant concentration in the aqueous composition is about 4.0% w/w. In other embodiments, the total surfactant concentration in the aqueous composition is about 4.5% w/w. In other embodiments, the total surfactant concentration in the aqueous composition is about 5.0% w/w. In other embodiments, the total surfactant concentration in the aqueous composition is about 5.5% w/w. In other embodiments, the total surfactant concentration in the aqueous composition is about 6.0% w/w. In other embodiments, the total surfactant concentration in the aqueous composition is about 6.5% w/w. In other embodiments, the total surfactant concentration in the aqueous composition is about 7.0% w/w. In other embodiments, the total surfactant concentration in the aqueous composition is about 7.5% w/w. In other embodiments, the total surfactant concentration in the aqueous composition is about 8.0% w/w. In other embodiments, the total surfactant concentration in the aqueous composition is about 9.0% w/w. In other embodiments, the total surfactant concentration in the aqueous composition is about 10% w/w.

In some embodiments, the concentration of the compound of Formula I or II is about 0.1%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.15%. In some further embodiments, the concentration of the co-surfactant is about 0.05%.

In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.20%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.25%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.30%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.35%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.40%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.45%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.50%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.55%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.60%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.65%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.70%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.75%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.80%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.85%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.90%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 0.95%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 1.0%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 1.25%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 1.50%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 1.75%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 2%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 3%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 4%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In some embodiments, the concentration of the compound of Formula I or II is about 5%. In some further embodiments, the concentration of the co-surfactant is about 0.05%. In some further embodiments, the concentration of the co-surfactant is about 0.10%. In some further embodiments, the concentration of the co-surfactant is about 0.15%. In some further embodiments, the concentration of the co-surfactant is about 0.20%. In some further embodiments, the concentration of the co-surfactant is about 0.25%. In some further embodiments, the concentration of the co-surfactant is about 0.30%. In some further embodiments, the concentration of the co-surfactant is about 0.35%. In some further embodiments, the concentration of the co-surfactant is about 0.40%. In some further embodiments, the concentration of the co-surfactant is about 0.45%. In some further embodiments, the concentration of the co-surfactant is about 0.50%. In some further embodiments, the concentration of the co-surfactant is about 0.55%. In some further embodiments, the concentration of the co-surfactant is about 0.60%. In some further embodiments, the concentration of the co-surfactant is about 0.65%. In some further embodiments, the concentration of the co-surfactant is about 0.70%. In some further embodiments, the concentration of the co-surfactant is about 0.75%. In some further embodiments, the concentration of the co-surfactant is about 0.80%. In some further embodiments, the concentration of the co-surfactant is about 0.85%. In some further embodiments, the concentration of the co-surfactant is about 0.90%. In some further embodiments, the concentration of the co-surfactant is about 0.95%. In some further embodiments, the concentration of the co-surfactant is about 1.0%. In some further embodiments, the concentration of the co-surfactant is about 1.25%. In some further embodiments, the concentration of the co-surfactant is about 1.5%. In some further embodiments, the concentration of the co-surfactant is about 1.75%. In some further embodiments, the concentration of the co-surfactant is about 2%. In some further embodiments, the concentration of the co-surfactant is about 3%. In some further embodiments, the concentration of the co-surfactant is about 4%. In some further embodiments, the concentration of the co-surfactant is about 5%.

In certain embodiments, the aqueous compositions can comprise a first surfactant and a second surfactant. In certain cases, the first surfactant can comprise an alkoxy sulfate surfactant and the second surfactant can comprise an olefin sulfonate surfactant. For example, is some embodiments, the aqueous composition can comprise (i) a compound defined by Formula I or II (e.g., 0.05% to 1% by weight of a compound defined by Formula I or II); a $C_{10}$-$C_{30}$ internal olefin sulfate (IOS) or a $C_8$-$C_{30}$ alkyl benzene sulfonate (ABS) (e.g., 0.05% to 1% by weight); and an alkoxy sulfate surfactant defined by the formula below

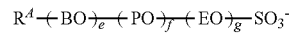

or acid or salt thereof, wherein $R^4$ is $C_8$-$C_{36}$ alkyl group; BO represents —$CH_2$—CH(ethyl)-O—; PO represents —$CH_2$—CH(methyl)-O—; EO represents —$CH_2$—$CH_2$—O—; and e, f and g are each independently integers from 0 to 50, with the proviso that at least one of e, f, and g is not zero (e.g., 0.05% to 1% by weight). In some embodiments, at least one of e and f is not zero. In one embodiment, the alkoxy sulfate surfactant can be $C_{13}$-$_{13}$PO-sulfate (i.e., an unsubstituted $C_{13}$ alkyl attached to 13 —$CH_2$—CH(methyl)-O— linkers, in turn attached to —$SO_3^-$ or acid or salt thereof including metal cations such as sodium) and the olefin sulfonate surfactant can be $C_{20}$-$C_{24}$ IOS.

In some embodiments, the aqueous compositions can further include a viscosity enhancing water-soluble polymer. In some embodiments, the water-soluble polymer may be a biopolymer such as xanthan gum or scleroglucan, a synthetic polymer such as polyacryamide, hydrolyzed polyarcrylamide or co-polymers of acrylamide and acrylic acid, 2-acrylamido 2-methyl propane sulfonate or N-vinyl pyrrolidone, a synthetic polymer such as polyethylene oxide, or any other high molecular weight polymer soluble in water or brine. In some embodiments, the polymer is polyacrylamide (PAM), partially hydrolyzed polyacrylamides (HPAM), and copolymers of 2-acrylamido-2-methylpropane sulfonic acid or sodium salt or mixtures thereof, and polyacrylamide (PAM) commonly referred to as AMPS copolymer and mixtures of the copolymers thereof. In one embodiment, the viscosity enhancing water-soluble polymer is polyacrylamide or a co-polymer of polyacrylamide. In one embodiment, the viscosity enhancing water-soluble polymer is a partially (e.g. 20%, 25%, 30%, 35%, 40%, 45%) hydrolyzed anionic polyacrylamide. In some further embodiment, the viscosity enhancing water-soluble polymer has a molecular weight of approximately about $8\times10^6$ Daltons. In some other further embodiment, the viscosity enhancing water-soluble polymer has a molecular weight of approximately about $18\times10^6$ Daltons. Non-limiting examples of commercially available polymers useful for the invention including embodiments provided herein are Florpaam 3330S and Florpaam 3360S. Molecular weights of the polymers may range from about 10,000 Daltons to about 20,000,000 Daltons. In some embodiments, the viscosity enhancing water-soluble polymer is used in the range of about 500 to about 5000 ppm concentration, such as from about 1000 to 2000 ppm (e.g., in order to match or exceed the reservoir oil viscosity under the reservoir conditions of temperature and pressure).

In some embodiments, the aqueous compositions can further include an alkali agent. An alkali agent as provided herein can be a basic, ionic salt of an alkali metal (e.g., lithium, sodium, potassium) or alkaline earth metal element (e.g., magnesium, calcium, barium, radium). Examples of suitable alkali agents include, for example, NaOH, KOH, LiOH, $Na_2CO_3$, $NaHCO_3$, Na-metaborate, Na silicate, Na orthosilicate, Na acetate or $NH_4OH$. The aqueous composition may include seawater, or fresh water from an aquifer, river or lake. In some embodiments, the aqueous composition includes hard brine water or soft brine water. In some further embodiments, the water is soft brine water. In some further embodiments, the water is hard brine water. Where the aqueous composition includes soft brine water, the aqueous composition can further include an alkaline agent. In soft brine water the alkaline agent can provide for enhanced soap generation from the active oils, lower surfactant adsorption to the solid material (e.g., rock) in the reservoir and increased solubility of viscosity enhancing water soluble polymers.

The alkali agent can be present in the aqueous composition at a concentration from about 0.1% w/w to about 10% w/w. The combined amount of alkali agent and compound provided herein (e.g., compound of Formula I or II) present in the aqueous composition provided herein can be approximately equal to or less than about 10% w/w. In some embodiments, the total concentration of alkali agent (i.e., the total amount of alkali agent within the aqueous compositions and emulsion compositions provided herein) in is from about 0.05% w/w to about 5% w/w. In other embodiments, the total alkali agent concentration in the aqueous composition is from about 0.25% w/w to about 5% w/w. In other embodiments, the total alkali agent concentration in the aqueous composition is about 0.5% w/w. In other embodiments, the total alkali agent concentration in the aqueous composition is about 0.75% w/w. In other embodiments, the total alkali agent concentration in the aqueous composition is about 1% w/w. In other embodiments, the total alkali agent concentration in the aqueous composition is about 1.25% w/w. In other embodiments, the total alkali agent concentration in the aqueous composition is about 1.50% w/w. In other embodiments, the total alkali agent concentration in the aqueous composition is about 1.75% w/w. In other embodiments, the total alkali agent concentration in the aqueous composition is about 2% w/w. In other embodiments, the total alkali agent concentration in the aqueous composition is about 2.25% w/w. In other embodiments, the total alkali agent concentration in the aqueous composition is about 2.5% w/w. In other embodiments, the total alkali agent concentration in the aqueous composition is about 2.75% w/w. In other embodiments, the total alkali agent concentration in the aqueous composition is about 3% w/w. In other embodiments, the total alkali agent concentration in the aqueous composition is about 3.25% w/w. In other embodiments, the total alkali agent concentration in the aqueous composition is about 3.5% w/w. In other embodiments, the total alkali agent concentration in the aqueous composition is about 3.75% w/w. In other embodiments, the total alkali agent concentration in the aqueous composition is about 4% w/w. In other embodiments, the total alkali agent concentration in the aqueous composition is about 4.25% w/w. In other embodiments, the total alkali agent concentration in the aqueous composition is about 4.5% w/w. In other embodiments, the total alkali agent concentration in the aqueous composition is about 4.75% w/w. In other embodiments, the total alkali agent concentration in the aqueous composition is about 5.0% w/w. In some embodiments, the alkali agent can be present in the aqueous compositions in an effective amount to afford an aqueous composition having a pH of from 10 to 12 (e.g., 10.5 to 11.5).

In some embodiments, the aqueous compositions can further include a co-solvent. In embodiments, the co-solvent is an alcohol, alcohol ethoxylate, glycol ether, glycols, or glycerol. The aqueous compositions provided herein may include more than one co-solvent. Thus, in embodiments, the aqueous composition includes a plurality of different co-solvents. Where the aqueous composition includes a plurality of different co-solvents, the different co-solvents can be distinguished by their chemical (structural) properties. For example, the aqueous composition may include a first co-solvent, a second co-solvent and a third co-solvent, wherein the first co-solvent is chemically different from the second and the third co-solvent, and the second co-solvent is chemically different from the third co-solvent. In embodiments, the plurality of different co-solvents includes at least two different alcohols (e.g., a $C_1$-$C_6$ alcohol and a $C_1$-$C_4$ alcohol). In embodiments, the aqueous composition includes a $C_1$-$C_6$ alcohol and a $C_1$-$C_4$ alcohol. In embodiments, the plurality of different co-solvents includes at least two different alkoxy alcohols (e.g., a $C_1$-$C_6$ alkoxy alcohol and a $C_1$-$C_4$ alkoxy alcohol). In embodiments, the aqueous composition includes a $C_1$-$C_6$ alkoxy alcohol and a $C_1$-$C_4$ alkoxy alcohol. In embodiments, the plurality of different co-solvents includes at least two co-solvents selected from the group consisting of alcohols, alkyl alkoxy alcohols and phenyl alkoxy alcohols. For example, the plurality of different co-solvents may include an alcohol and an alkyl alkoxy alcohol, an alcohol and a phenyl alkoxy alcohol, or an alcohol, an alkyl alkoxy alcohol and a phenyl alkoxy alcohol. The alkyl alkoxy alcohols or phenyl alkoxy alcohols provided herein have a hydrophobic portion (alkyl or aryl chain), a hydrophilic portion (e.g., an alcohol) and optionally an alkoxy (ethoxylate or propoxylate) portion. Thus, in embodiments, the co-solvent is an alcohol, alkoxy alcohol, glycol ether, glycol or glycerol. Suitable co-solvents are known in the art, and include, for example, co-surfactants described in U.S. Patent Application Publication No. 2013/0281327 which is hereby incorporated herein in its entirety In some embodiments, a co-solvent can be present in an amount sufficient to increase the solubility of the small hydrophobe anionic surfactant in the aqueous phase realtive to the absence of the co-solvent. In other words, in the presence of a sufficient amount of the co-solvent, the solubility of the small hydrophobe anionic surfactant in the aqueous phase is higher than in the absence of the co-solvent. In embodiments, the co-solvent can be present in an amount sufficient to increase the solubility of the co-surfactant in the aqueous phase relative to the absence of the co-solvent. Thus, in the presence of a sufficient amount of the co-solvent the solubility of the co-surfactant in the aqueous phase can be higher than in the absence of the co-solvent. In embodiments, the co-solvent can be present in an amount sufficient to decrease the viscosity of an emulsion formed from the composition relative to the absence of the co-solvent.

In other embodiments, the aqueous composition can be substantially free of co-solvents (e.g., the composition can include less than 0.05% by weight co-solvents, based on the total weight of the composition).

In some embodiments, the aqueous composition can further include a gas. For instance, the gas may be combined with the aqueous composition to reduce its mobility by decreasing the liquid flow in the pores of the solid material (e.g., rock). In some embodiments, the gas may be supercritical carbon dioxide, nitrogen, natural gas or mixtures of these and other gases.

In some embodiments, the aqueous composition can have a pH of at least 7 (e.g., a pH of at least 7.5, a pH of at least 8, a pH of at least 8.5, a pH of at least 9, a pH of at least 9.5, a pH of at least 10, a pH of at least 10.5, a pH of at least 11, a pH of at least 11.5, or a pH of at least 12.5). In some embodiments, the aqueous composition can have a pH of 13 or less (e.g., a pH of 12.5 or less, a pH of 12 or less, a pH of 11.5 or less, a pH of 11 or less, a pH of 10.5 or less, a pH of 10 or less, a pH of 9.5 or less, a pH of 9 or less, a pH of 8.5 or less, a pH of 8 or less, or a pH of 7.5 or less). The aqueous composition can have a pH ranging from any of the minimum values described above to any of the maximum values described above. For example, the aqueous composition can have a pH of from 7 to 13 (e.g., from 10 to 12, or from 10.5 to 11.5).

In some embodiments, the aqueous composition can have a salinity of at least 5,000 ppm. In other embodiments, the aqueous composition has a salinity of at least 50,000 ppm. In other embodiments, the aqueous composition has a salinity of at least 100,000 ppm. In other embodiments, the aqueous composition has a salinity of at least 250,000 ppm. The total range of salinity (total dissolved solids in the brine) is 100 ppm to saturated brine (about 260,000 ppm). The aqueous composition may include seawater, brine or fresh water from an aquifer, river or lake. The aqueous combination may further include salt to increase the salinity. In some embodiments, the salt is NaCl, KCl, $CaCl_2$, $MgCl_2$, $CaSO_4$, Na acetate or $Na_2CO_3$.

In some embodiments, the aqueous composition can have a temperature of at least 20° C. (e.g., at least 30° C., at least 40° C., at least 50° C., at least 60° C., at least 70° C., at least 80° C., at least 90° C., at least 100° C., or at least 110° C.). The aqueous composition can have a temperature of 120° C. or less (e.g., 110° C. or less, 100° C. or less, 90° C. or less, 80° C. or less, 70° C. or less, 60° C. or less, 50° C. or less, 40° C. or less, or 30° C. or less). In some embodiments, the aqueous composition can have a temperature of greater than 120° C.

The aqueous composition can have a temperature ranging from any of the minimum values described above to any of the maximum values described above. For example, the aqueous composition can have a temperature of from 20° C. to 120° C. (e.g., from 50° C. to 120° C., or from 80° C. to 120° C.).

In some embodiments, the aqueous composition can have a viscosity of between 20 mPas and 100 mPas at 20° C. The viscosity of the aqueous solution may be increased from 0.3 mPas to 1, 2, 10, 20, 100 or even 1000 mPas by including a water-soluble polymer. As mentioned above, the apparent viscosity of the aqueous composition may be increased with a gas (e.g., a foam forming gas) as an alternative to the water-soluble polymer.

Also provided are emulsions comprising (i) the a small hydrophobe anionic surfactant or an aqueous composition described herein and (ii) unrefined petroleum. In some embodiments, the emulsion composition can be a microemulsion. A "microemulsion" as referred to herein is a thermodynamically stable mixture of oil, water and surfactants that may also include additional components such as co-solvents, electrolytes, alkali and polymers. In contrast, a "macroemulsion" as referred to herein is a thermodynamically unstable mixture of oil and water that may also include additional components. The emulsion composition provided herein may be an oil-in-water emulsion, wherein the surfactant forms aggregates (e.g., micelles) where the hydrophilic part of the surfactant molecule(s) contacts the aqueous phase of the emulsion and the lipophilic part contacts the oil phase of the emulsion. Thus, in some embodiments, the surfactant(s) form part of the aqueous part of the emulsion. And in other embodiments, the surfactant(s) form part of the oil phase of the emulsion. In yet another embodiment, the surfactant(s) form part of an interface between the aqueous phase and the oil phase of the emulsion.

In other embodiments, the oil and water solubilization ratios are insensitive to the combined concentration of divalent metal cations (e.g., $Ca^{2+}$ and $Mg^{2+}$) within the emulsion composition. In other embodiments, the oil and water solubilization ratios are insensitive to the salinity of the water or to all of the specific electrolytes contained in the water. The term "insensitive" used in the context of this paragraph means that the solubilization ratio tends not to change (e.g., tends to remain constant) as the concentration of divalent metal cations and/or salinity of water changes. In some embodiments, the change in the solubilization ratios are less than 5%, 10%, 20%, 30%, 40%, or 50% over a divalent metal cation concentration range of 10 ppm, 100 ppm, 1000 ppm or 10,000 ppm. In another embodiment, the change in the solubilization ratios are less than 5%, 10%, 20%, 30%, 40%, or 50% over a salinity concentration range of 10 ppm, 100 ppm, 1000 ppm or 10,000 ppm.

Methods

In another aspect, a method of displacing a hydrocarbon material in contact with a solid material is provided. The method includes contacting a hydrocarbon material with a compound as described herein (e.g. a short hydrophobe anionic surfactant), wherein the hydrocarbon material is in contact with a solid material. The hydrocarbon material is allowed to separate from the solid material thereby displacing the hydrocarbon material in contact with the solid material.

In other embodiments, the hydrocarbon material is unrefined petroleum (e.g., in a petroleum reservoir). In some further embodiments, the unrefined petroleum is a light oil. A "light oil" as provided herein is an unrefined petroleum with an API gravity greater than 30. In some embodiments, the API gravity of the unrefined petroleum is greater than 30. In other embodiments, the API gravity of the unrefined petroleum is greater than 40. In some embodiments, the API gravity of the unrefined petroleum is greater than 50. In other embodiments, the API gravity of the unrefined petroleum is greater than 60. In some embodiments, the API gravity of the unrefined petroleum is greater than 70. In other embodiments, the API gravity of the unrefined petroleum is greater than 80. In some embodiments, the API gravity of the unrefined petroleum is greater than 90. In other embodiments, the API gravity of the unrefined petroleum is greater than 100. In some other embodiments, the API gravity of the unrefined petroleum is between 30 and 100.

The solid material may be a natural solid material (i.e., a solid found in nature such as rock). The natural solid material may be found in a petroleum reservoir. In some embodiments, the method is an enhanced oil recovery method. Enhanced oil recovery methods are well known in the art. A general treatise on enhanced oil recovery methods is Basic Concepts in Enhanced Oil Recovery Processes edited by M. Baviere (published for SCI by Elsevier Applied Science, London and New York, 1991). For example, in an enhanced oil recovery method, the displacing of the unrefined petroleum in contact with the solid material is accomplished by contacting the unrefined with a compound provided herein, wherein the unrefined petroleum is in contact with the solid material. The unrefined petroleum may be in an oil reservoir. The compound or composition provided herein can be pumped into the reservoir in accordance with known enhanced oil recovery parameters. The compound can be pumped into the reservoir as part of the aqueous compositions provided herein and, upon contacting the unrefined petroleum, form an emulsion composition provided herein.

In some embodiments, the natural solid material can be rock or regolith. The natural solid material can be a geological formation such as clastics or carbonates. The natural solid material can be either consolidated or unconsolidated material or mixtures thereof. The hydrocarbon material may be trapped or confined by "bedrock" above or below the natural solid material. The hydrocarbon material may be found in fractured bedrock or porous natural solid material. In other embodiments, the regolith is soil.

In some embodiments, an emulsion forms after the contacting step. The emulsion thus formed can be the emulsion described above. In some embodiments, the method includes allowing an unrefined petroleum acid within the unrefined petroleum material to enter into the emulsion, thereby converting the unrefined petroleum acid into a surfactant. In other words, where the unrefined petroleum acid converts into a surfactant it is mobilized and therefore separates from the solid material.

In another aspect, a method of converting (e.g., mobilizing) an unrefined petroleum acid into a surfactant is provided. The method includes contacting a petroleum material with an aqueous composition thereby forming an emulsion in contact with the petroleum material, wherein the aqueous composition includes the compound described herein (e.g. a small hydrophobe anionic surfactant) and a co-surfactant. Thus, in some embodiments, the aqueous composition is the aqueous composition described above. An unrefined petroleum acid within the unrefined petroleum material is allowed to enter into the emulsion, thereby converting the unrefined petroleum acid into a surfactant. In some embodiments, the reactive petroleum material is in a petroleum reservoir. In some embodiments, as described above and as is generally known in the art, the unrefined petroleum acid is a naphthenic acid. In some embodiments, as described above and as is generally known in the art, the unrefined petroleum acid is a mixture of naphthenic acid. In some embodiments, the aqueous composition further includes an alkali agent.

In another aspect, a method of making a compound as described herein (e.g. a small hydrophobe anionic surfactant) is provided. The methods can include contacting a suitable alcohol precursor for the small hydrophobe anionic surfactant (e.g., a $C_7$-$C_{12}$ alcohol) with a propylene oxide thereby forming a first alkoxylated hydrophobe. The first alkoxylated hydrophobe can subsequently be contacted with an ethylene oxide thereby forming a second alkoxylated hydrophobe. The second alkoxylated hydrophobe can then be contacted with one or more anionic functional groups thereby forming a small hydrophobe anionic surfactant. In some embodiments, the contacting is performed at an elevated temperature.

By way of non-limiting illustration, examples of certain embodiments of the present disclosure are given below.

EXAMPLES

The examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, percents associated with components of compositions are percents by weight, based on the total weight of the composition including the components, temperature is in ° C. or is at ambient temperature, and pressure is at or near atmospheric.

Phase Behavior Procedures

Phase Behavior Screening: Phase behavior studies have been used to characterize chemicals for EOR. There are many benefits in using phase behavior as a screening method. Phase Behavior studies are used to determine, measure or observe characteristics related to chemical performance such as the following examples but are not limited to these examples: (1) the effect of electrolytes; (2) oil solubilization and IFT reduction, (3) microemulsion densities; (4) microemulsion viscosities; (5) coalescence times; (6) optimal surfactant-co-solvent formulations; and/or (7) optimal properties for recovering oil from cores and reservoirs.

Thermodynamically stable phases can form with oil, water and surfactant mixtures. Surfactants form micellar structures at concentrations at or above the critical micelle concentration (CMC). The emulsion coalesces into a separate phase at the oil-water interface and is referred to as a microemulsion. A microemulsion is a surfactant-rich distinct phase consisting of surfactant, oil and water and possibly co-solvents and other components. This phase is thermodynamically stable in the sense that it will return to the same phase volume at a given temperature. Some workers in the past have added additional requirements, but for the purposes of this engineering study, the only requirement will be that the microemulsion is a thermodynamically stable phase.

The phase transition is examined by keeping all variables fixed except for the scanning variable. The scan variable is changed over a series of pipettes and may include, but is not limited to, salinity, temperature, chemical (surfactant, alcohol, electrolyte), oil, which is sometimes characterized by its equivalent alkane carbon number (EACN), and surfactant structure, which is sometimes characterized by its hydrophilic-lipophilic balance (HLB). The phase transition was first characterized by Winsor (1954) into three regions: Type I-excess oleic phase, Type III-aqueous, microemulsion and oleic phases, and the Type II-excess aqueous phase. The phase transition boundaries and some common terminology are described as follows: Type I to III-lower critical salinity, Type III to II-upper critical salinity, oil solubilization ratio (Vo/Vs), water solubilization ratio (Vw/Vs), the solubilization value where the oil and water solubilization ratios are equal is called the Optimum Solubilization Ratio (σ*), and the electrolyte concentration where the optimum solubilization ratio occurs is referred to as the Optimal Salinity (S*).

Determining Interfacial Tension

Efficient use of time and lab resources can lead to valuable results when conducting phase behavior scans. A correlation between oil and water solubilization ratios and interfacial tension was suggested by Healy and Reed (1976) and a theoretical relationship was later derived by Chun Huh (1979). Lowest oil-water IFT occurs at optimum solubilization as shown by the Chun Huh theory. This is equated to an interfacial tension through the Chun Huh equation, where IFT varies with the inverse square of the solubilization ratio:

$$\gamma = \frac{C}{\sigma^2}$$

For most crude oils and microemulsions, C=0.3 is a good approximation. Therefore, a quick and convenient way to estimate IFT is to measure phase behavior and use the Chun-Huh equation to calculate IFT. The IFT between microemulsions and water and/or oil can be very difficult and time consuming to measure and is subject to larger errors, so using the phase behavior approach to screen hundreds of combinations of surfactants, co-surfactants, co-solvents, electrolytes, oil, and so forth is not only simpler and faster, but avoids the measurement problems and errors associated with measuring IFT especially of combinations that show complex behavior (gels and so forth) and will be screened out anyway. Once a good formulation has been identified, then it is still a good idea to measure IFT.

Equipment

Phase behavior experiments are created with the following materials and equipment.

Mass Balance: Mass balances are used to measure chemicals for mixtures and determine initial saturation values of cores.

Water Deionizer: Deionized (DI) water is prepared for use with all the experimental solutions using a Nanopure™ filter system. This filter uses a recirculation pump and monitors the water resistivity to indicate when the ions have been removed. Water is passed through a 0.45 micron filter to eliminate undesired particles and microorganisms prior to use.

Borosilicate Pipettes: Standard 5 mL borosilicate pipettes with 0.1 mL markings are used to create phase behavior scans as well as run dilution experiments with aqueous solutions. Ends are sealed using a propane and oxygen flame.

Pipette Repeater: An Eppendorf Repeater Plus™ instrument is used for most of the pipetting. This is a handheld dispenser calibrated to deliver between 25 microliter and 1 ml increments. Disposable tips are used to avoid contamination between stocks and allow for ease of operation and consistency.

Propane-oxygen Torch: A mixture of propane and oxygen gas is directed through a Bernz-O-Matic flame nozzle to create a hot flame about ½ inch long. This torch is used to flame-seal the glass pipettes used in phase behavior experiments.

Convection Ovens: Several convection ovens are used to incubate the phase behaviors and core flood experiments at the reservoir temperatures. The phase behavior pipettes are primarily kept in Blue M and Memmert ovens that are monitored with mercury thermometers and oven temperature gauges to ensure temperature fluctuations are kept at a minimal between recordings. A large custom built flow oven was used to house most of the core flood experiments and enabled fluid injection and collection to be done at reservoir temperature.

pH Meter: An ORION research model 701/digital ion analyzer with a pH electrode is used to measure the pH of most aqueous samples to obtain more accurate readings. This is calibrated with 4.0, 7.0 and 10.0 pH solutions. For rough measurements of pH, indicator papers are used with several drops of the sampled fluid.

Phase Behavior Calculations

The oil and water solubilization ratios are calculated from interface measurements taken from phase behavior pipettes. These interfaces are recorded over time as the mixtures approached equilibrium and the volume of any macroemulsions that initially formed decreased or disappeared.

Phase Behavior Methodology

The methods for creating, measuring and recording observations are described in this section. Scans are made using a variety of electrolyte mixtures described below. Oil is added to most aqueous surfactant solutions to see if a microemulsion formed, how long it took to form and equilibrate if it formed, what type of microemulsion formed and some of its properties such as viscosity. However, the behavior of aqueous mixtures without oil added is also important and is also done in some cases to determine if the aqueous solution is clear and stable over time, becomes cloudy or separated into more than one phase.

Preparation of samples. Phase behavior samples are made by first preparing surfactant stock solutions and combining them with brine stock solutions in order to observe the behavior of the mixtures over a range of salinities. All the experiments are created at or above 0.1 wt % active surfactant concentration, which is above the typical CMC of the surfactant.

Solution Preparation. Surfactant stocks are based on active weight-percent surfactant (and co-surfactant when incorporated). The masses of surfactant, co-surfactant, co-solvent and de-ionized water (DI) are measured out on a balance and mixed in glass jars using magnetic stir bars. The order of addition is recorded on a mixing sheet along with actual masses added and the pH of the final solution. Brine solutions are created at the necessary weight percent concentrations for making the scans.

Surfactant Stock. The chemicals being tested are first mixed in a concentrated stock solution that usually consisted of a primary surfactant, co-solvent and/or co-surfactant along with de-ionized water. The quantity of chemical added is calculated based on activity and measured by weight percent of total solution. Initial experiments are at about 1-3% active surfactant so that the volume of the middle microemulsion phase would be large enough for accurate measurements assuming a solubilization ratio of at least 10 at optimum salinity.

Polymer Stock. Often these stocks were quite viscous and made pipetting difficult so they are diluted with de-ionized water accordingly to improve ease of handling. Mixtures with polymer are made only for those surfactant formulations that showed good behavior and merited additional study for possible testing in core floods. Consequently, scans including polymer are limited since they are done only as a final evaluation of compatibility with the surfactant.

Pipetting Procedure. Phase behavior components are added volumetrically into 5 ml pipettes using an Eppendorf Repeater Plus or similar pipetting instrument. Surfactant and brine stocks are mixed with DI water into labeled pipettes and brought to temperature before agitation. Almost all of the phase behavior experiments are initially created with a water oil ratio (WOR) of 1:1, which involves mixing 2 ml of the aqueous phase with 2 ml of the evaluated crude oil or hydrocarbon, and different WOR experiments are mixed accordingly. The typical phase behavior scan consisted of 10-20 pipettes, each pipette being recognized as a data point in the series.

Order of Addition. Consideration must be given to the addition of the components since the concentrations are often several folds greater than the final concentration. Therefore, an order is established to prevent any adverse effects resulting from surfactant or polymer coming into direct contact with the concentrated electrolytes. The desired sample compositions are made by combining the stocks in the following order: (1) Electrolyte stock(s); (2) De-ionized water; (3) Surfactant stock; (4) Polymer stock; and (5) Crude oil or hydrocarbon. Any air bubbles trapped in the bottom of the pipettes are tapped out (prior to the addition of surfactant to avoid bubbles from forming).

Initial Observations. Once the components are added to the pipettes, sufficient time is allotted to allow all the fluid to drain down the sides. Then aqueous fluid levels are recorded before the addition of oil. These measurements are marked on record sheets. Levels and interfaces are recorded on these documents with comments over several days and additional sheets are printed as necessary.

Sealing and Mixing. The pipettes are blanketed with argon gas to prevent the ignition of any volatile gas present by the flame sealing procedure. The tubes are then sealed with the propane-oxygen torch to prevent loss of additional volatiles when placed in the oven. Pipettes are arranged on the racks to coincide with the change in the scan variable. Once the phase behavior scan is given sufficient time to reach reservoir temperature (15-30 minutes), the pipettes are inverted several times to provide adequate mixing. Tubes are observed for low tension upon mixing by looking at droplet size and how uniform the mixture appeared. Then the solutions are allowed to equilibrate over time and interface levels are recorded to determine equilibration time and surfactant performance.

Measurements and Observations. Phase behavior experiments are allowed to equilibrate in an oven that is set to the reservoir temperature for the crude oil being tested. The fluid levels in the pipettes are recorded periodically and the trend in the phase behavior observed over time. Equilibrium behavior is assumed when fluid levels ceased to change within the margin of error for reading the samples.

Fluid Interfaces. The fluid interfaces are the most crucial element of phase behavior experiments. From them, the phase volumes are determined and the solubilization ratios are calculated. The top and bottom interfaces are recorded as the scan transitioned from an oil-in-water microemulsion to a water-in-oil microemulsion. Initial readings are taken one day after initial agitation and sometimes within hours of agitation if coalescence appeared to happen rapidly. Measurements are taken thereafter at increasing time intervals (for example, one day, four days, one week, two weeks, one month and so on) until equilibrium is reached or the experiment is deemed unessential or uninteresting for continued observation.

Figure 2A:
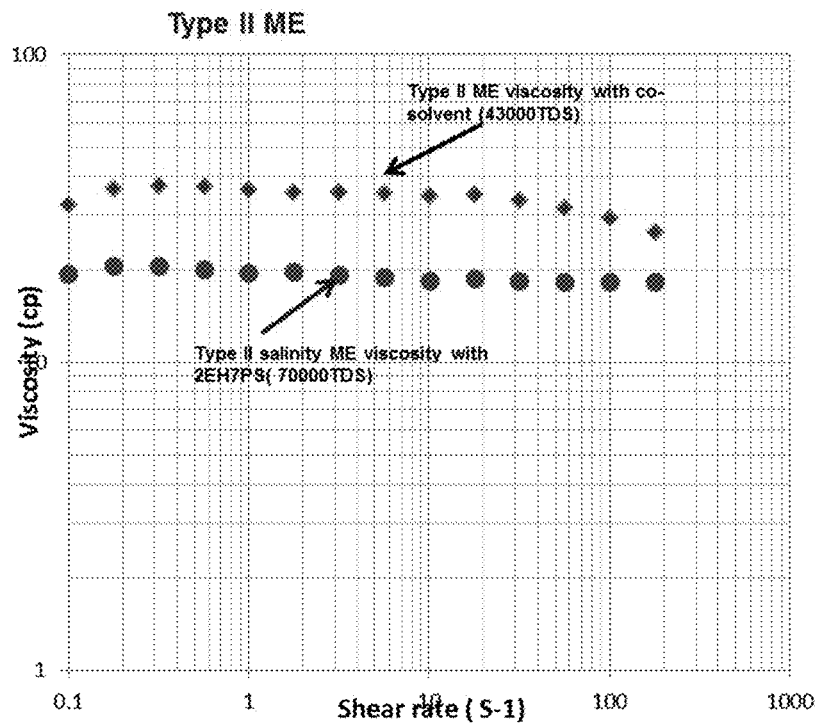
FIG. 2A is a plot comparing the apparent viscosity vs. shear rate at 24° C. of a Winsor type II microemulsion formed from Oil #1 and a surfactant formulation that includes 0.55% TDA-13PO-Sulfate, 0.2% C20-24 IOS, and 0.75% Phenol-2EO (43,000 ppm (TDS) of $Na_2CO_3$, diamond trace) and a Winsor type II microemulsion formed from Oil #1 and a surfactant formulation that includes 0.1% TDA-13PO-Sulfate, 0.2% C20-24 IOS, 0.2% TDA-45PO-10EO-Sulfate, and 0.25% 2-Ethylhexanol-7PO-Sulfate (70,000 ppm (TDS) of $Na_2CO_3$, circle trace).
Figure 2B:
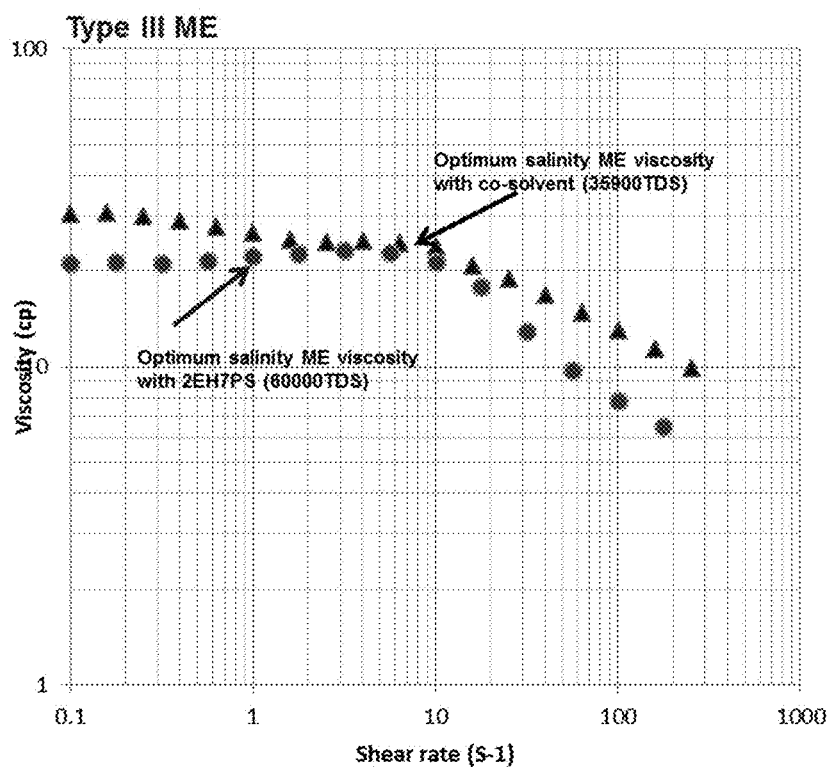
FIG. 2B is a plot comparing the apparent viscosity vs. shear rate at 24° C. of a Winsor type III microemulsion formed from Oil #1 and a surfactant formulation that includes 0.55% TDA-13PO-Sulfate, 0.2% C20-24 IOS, and 0.75% Phenol-2EO (35,900 ppm (TDS) of $Na_2CO_3$, triangle trace) and a Winsor type III microemulsion formed from Oil #1 and a surfactant formulation that includes 0.1% TDA-13PO-Sulfate, 0.2% C20-24 IOS, 0.2% TDA-45PO-10EO-Sulfate, and 0.25% 2-Ethylhexanol-7PO-Sulfate (60,000 ppm (TDS) of $Na_2CO_3$, circle trace).
Figure 3A:
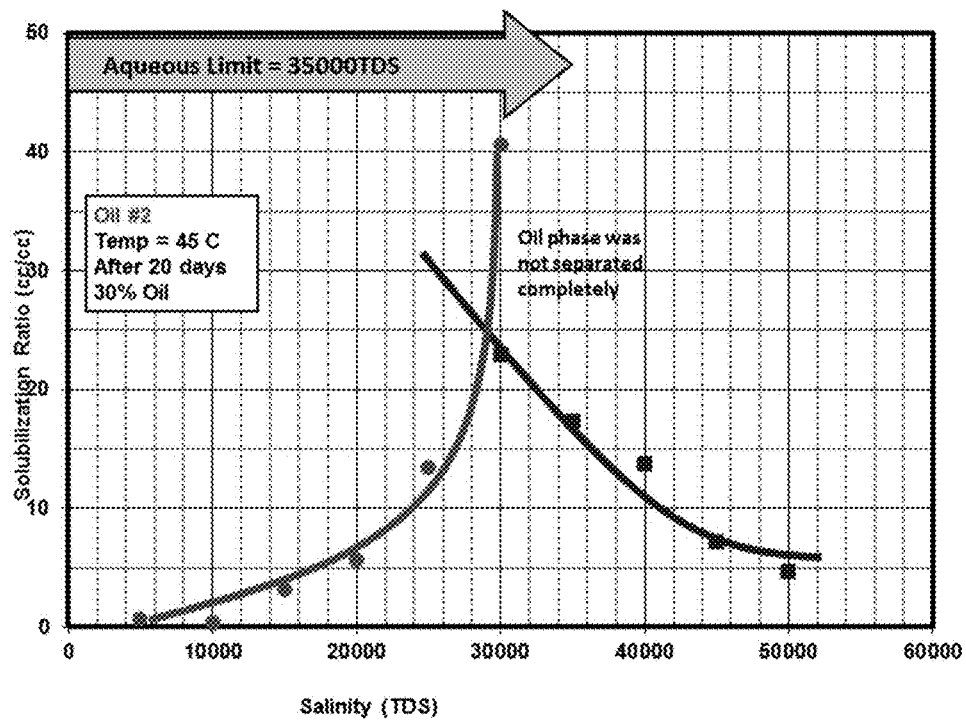
FIG. 3A is a plot of the solubilization ratios for light crude oil using a surfactant formulation that includes 0.5% TDA-13PO-Sulfate, 0.5% C20-24 IOS, and 1% TEGBE (2% total chemical content) with Oil #2 (30%) at 45° C. after 20 days. The arrow in the histogram pointing from left to right indicates the aqueous stability at 35,000 ppm (TDS) of $Na_2CO_3$.
Figure 3B:
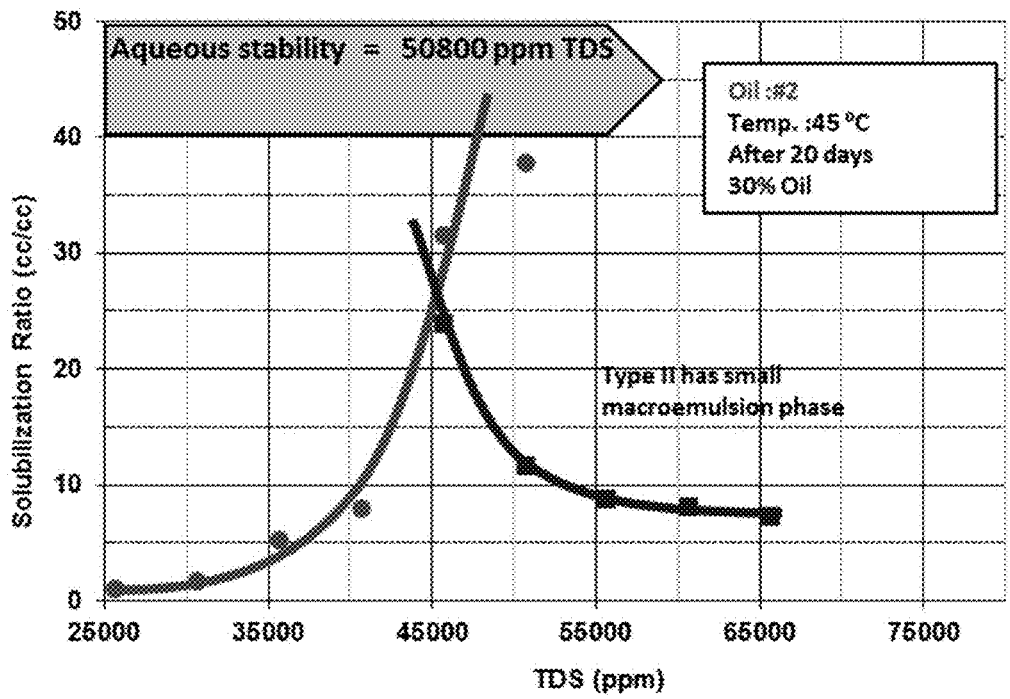
FIG. 3B is a plot of the solubilization ratios for light crude oil using a surfactant formulation that includes 0.3% TDA-45PO-10EO-Sulfate, 0.3% C20-24 IOS, and 0.4% 2-Ethylhexanol-7PO-Sulfate (1% total chemical content) with Oil #2 (30%) at 45° C. after 20 days. The arrow in the histogram pointing from left to right indicates the aqueous stability at 50,800 ppm (TDS) of $Na_2CO_3$.
Figure 4A:
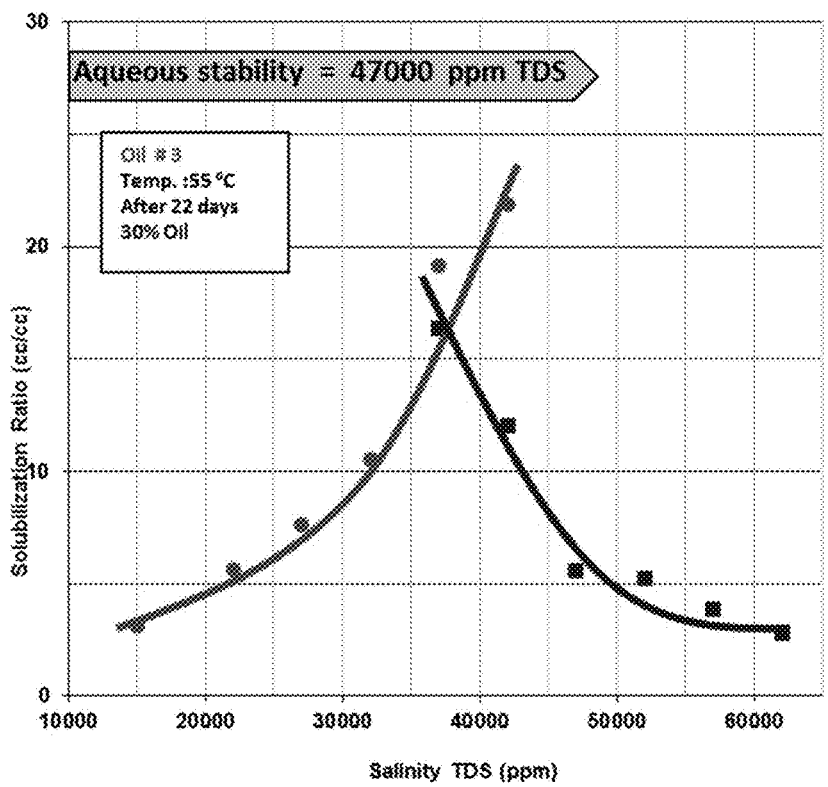
FIG. 4A is a plot of the solubilization ratios for light crude oil using a surfactant formulation that includes 0.4% TDA-7PO-Sulfate, 0.4% C19-23 IOS, 0.2% Ole-35PO-10EO-Sulfate, and 1.0% IBA-3EO (2% total chemical content) with Oil #3 (30%) at 55° C. after 22 days. The arrow in the histogram pointing from left to right indicates the aqueous stability at 47,000 ppm (TDS) of $Na_2CO_3$.
Figure 4B:
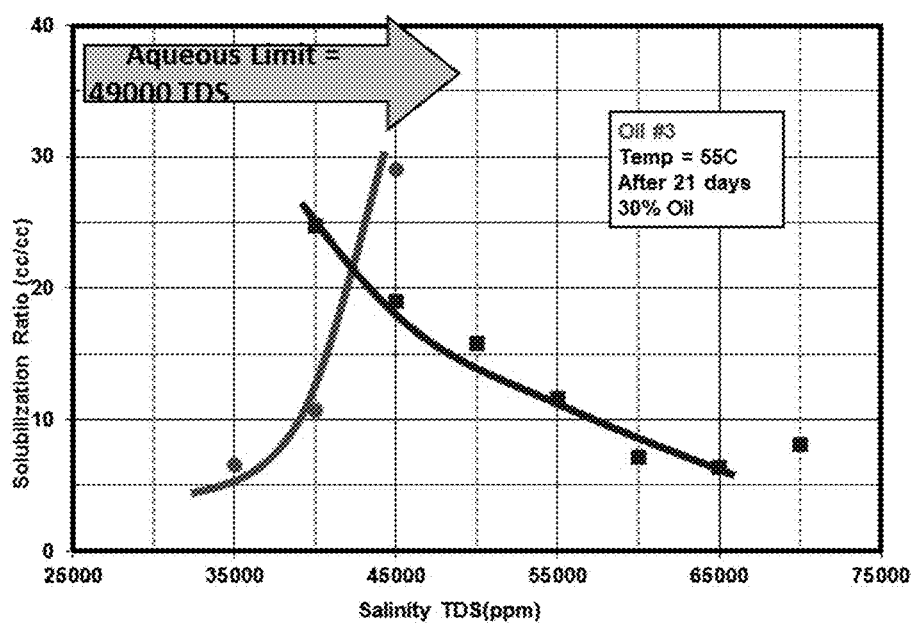
FIG. 4B is a plot of the solubilization ratios for light crude oil using a surfactant formulation that includes 0.4% C19-23 IOS, 0.2% Ole-35PO-10EO-Sulfate, and 0.4% 2-Ethylhexanol-7PO-Sulfate (1% total chemical content) with Oil #3 (30%) at 55° C. after 21 days. The arrow in the histogram pointing from left to right indicates the aqueous stability at 49,000 ppm (TDS) of $Na_2CO_3$.
Figure 5A:
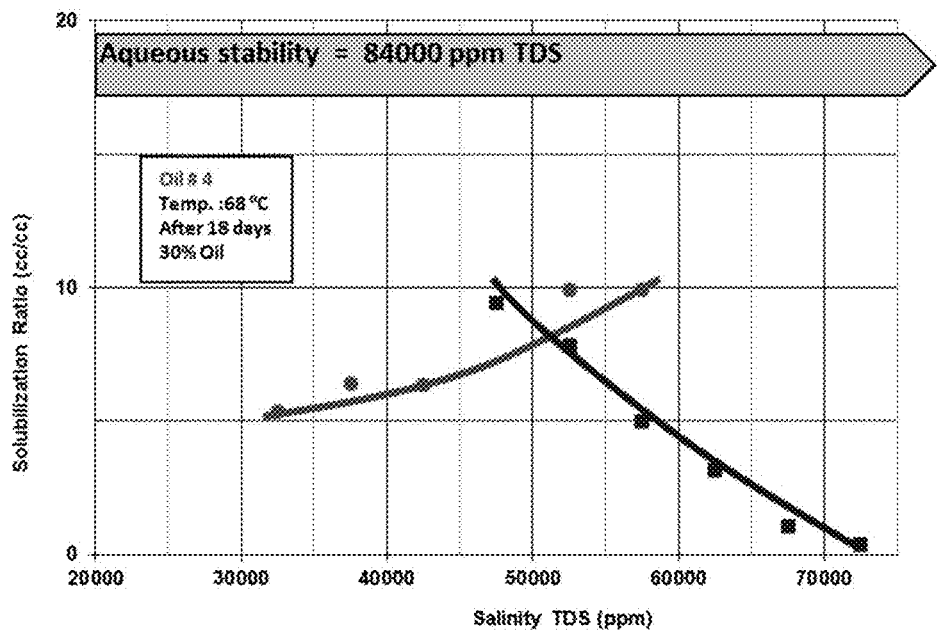
FIG. 5A is a plot of the solubilization ratios for light crude oil using a surfactant formulation that includes 0.5% TDA-45PO-10EO-Sulfate, 0.15% C15-18 IOS, 0.35% C19-23 IOS, and 1% Phenol-6EO (2% total chemical content) with Oil #4 (30%) at 68° C. after 18 days. The arrow in the histogram pointing from left to right indicates the aqueous stability at 84,000 ppm (TDS) of $Na_2CO_3$.
Figure 5B:
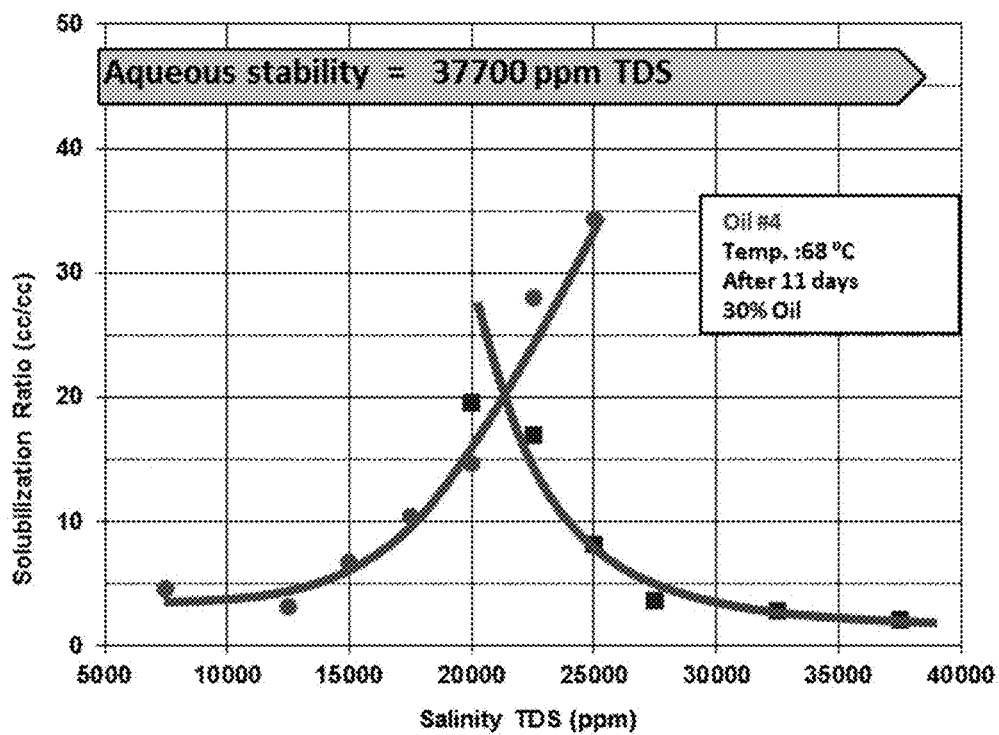
FIG. 5B is a plot of the solubilization ratios for light crude oil using a surfactant formulation that includes 0.2% C20-24 IOS, 0.3% Ole-45PO-30EO-COONa, and 0.5% 2-Ethylhexanol-7PO-Sulfate (1% total chemical content) with Oil #4 (30%) at 68° C. after 11 days. The arrow in the histogram pointing from left to right indicates the aqueous stability at 37,700 ppm (TDS) of $Na_2CO_3$.
Figure 6A:
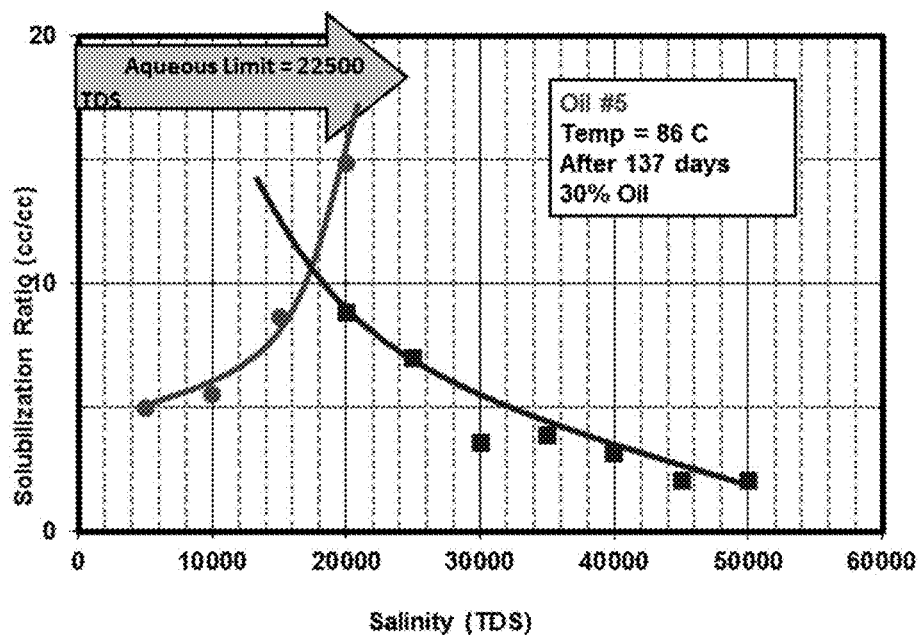
FIG. 6A is a plot of the solubilization ratios for light crude oil using a surfactant formulation that includes 0.5% TDA-7PO-Sulfate, 0.5% C20-24 IOS, and 0.5% TEGBE (1.5% total chemical content) with Oil #5 (30%) at 86° C. after 137 days. The arrow in the histogram pointing from left to right indicates the aqueous stability at 22,500 ppm (TDS) of $Na_2CO_3$.
Figure 6B:
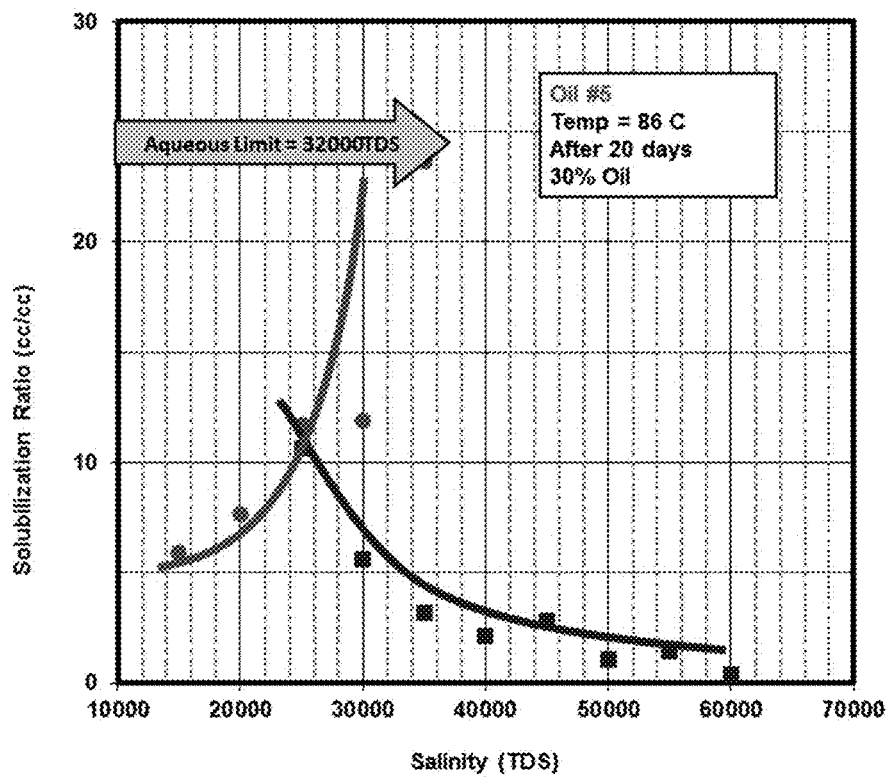
FIG. 6B is a plot of the solubilization ratios for light crude oil using a surfactant formulation that includes 0.25% C20-24 IOS, 0.25% TDA-35PO-20EO-Sulfate, and 0.5% 2-Ethylhexanol-7PO-Sulfate (1% total chemical content) with Oil #5 (30%) at 86° C. after 20 days. The arrow in the histogram pointing from left to right indicates the aqueous stability at 32,000 ppm (TDS) of $Na_2CO_3$.
Figure 7:
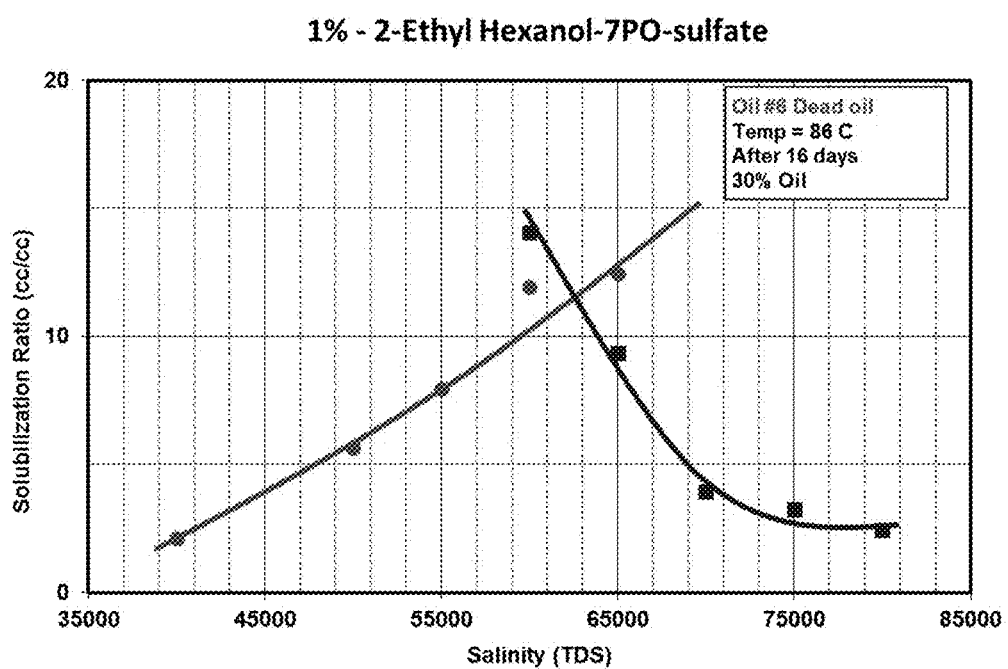
FIG. 7 is a plot of the solubilization ratios for light crude oil using 1% 2-Ethylhexanol-7PO-Sulfate with Oil #6 (30%) at 86° C. after 16 days.

Using the general methods described above, the phase behavior of five EOR formulations containing traditional co-solvents were compared to five EOR formulations containing the small hydrophobe anionic surfactants described herein. Five different example oils were used. The resulting solubilization ratios are shown in FIGS. 1A-B, 3A-B, 4A-B, 5A-B, and 6A-B. The influence of the small hydrophobe anionic surfactants described herein on microemulsion viscosity was also evaluated (FIGS. 2A-B).

These results demonstrate that the short hydrophobe anionic surfactants described herein can be used in EOR formulations to impart many beneficial properties generally afforded by co-solvents. For example, the short hydrophobe anionic surfactants can provide for faster equilibration, low microemulsion viscosity, and improved aqueous stability. In particular, the short hydrophobe anionic surfactants described herein can impart one or more of these desirable properties (e.g., lower microemulsion viscosity) while also decreasing interfacial tension. Thus, the short hydrophobe anionic surfactants described herein can be incorporated into EOR formulations to improve equilibration, increase solubilization ratio, provide a broad low interfacial tension region, decrease microemulsion viscosity, and combinations thereof. As the short hydrophobe anionic surfactants described herein can perform the dual role of surfactant and co-solvent in EOR formulations, the short hydrophobe anionic surfactants described herein can be used to prepare EOR formulations with lower amounts of co-solvent (or even EOR formulations that are substantially free from co-solvents).

The compounds, compositions, and methods of the appended claims are not limited in scope by the specific compounds, compositions, and methods described herein, which are intended as illustrations of a few aspects of the claims. Any compounds, compositions, and methods that are functionally equivalent are intended to fall within the scope of the claims. Various modifications of the compounds, compositions, and methods in addition to those shown and described herein are intended to fall within the scope of the appended claims. Further, while only certain representative compounds, compositions, and method steps disclosed herein are specifically described, other combinations of the compounds, compositions, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. An aqueous composition consisting of water, a compound defined by Formula I

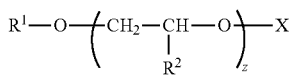

wherein
- $R^1$ is a $C_7$-$C_{12}$ alkyl group, an $R^3$-substituted aryl group, or an $R^3$-substituted cycloalkyl group;
- $R^2$ is independently hydrogen or methyl;
- $R^3$ is an alkyl group, wherein the alkyl group together with the aryl group or cycloalkyl group to which the alkyl group is attached comprise from 7 to 12 carbon atoms;
- z is an integer from 2 to 24;
- X is $-SO_3^-M^+$, $-SO_3H$, $-CH_2C(O)O^-M^+$, $-CH_2C(O)OH$; and
- $M^+$ is a cation, and
an additional surfactant,
wherein the compound of Formula I is present in the composition in an amount of from 0.05% to 2% by weight, based on the total weight of the composition, and
wherein a polymer, an alkali agent, a co-solvent, or a combination thereof are optionally present, wherein when the polymer is present, the polymer is selected from a biopolymer, a polyacrylamide, a hydrolyzed polyacrylamide or a copolymer thereof, N-vinyl pyrrolidone, polyethylene oxide, or a combination thereof.

2. The composition of claim 1, wherein z is from 2 to 15.

3. The composition of claim 1, wherein $R^1$ is a branched $C_7$-$C_{12}$ alkyl group.

4. The composition of claim 1, wherein $R^1$ is a 2-ethylhexyl group.

5. The composition of claim 1, wherein the compound is defined by Formula II

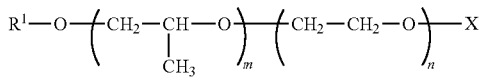

wherein
- $R^1$ is a $C_7$-$C_{12}$ alkyl group, an $R^3$-substituted aryl group, or an $R^3$-substituted cycloalkyl group;
- $R^3$ is an alkyl group, wherein the alkyl group together with the aryl group or cycloalkyl group to which the alkyl group is attached comprise from 7 to 12 carbon atoms;
- m is an integer from 2 to 24 and n is an integer from 0 to 22, with the proviso that m+n is from 2 to 24;
- X is $-SO_3^-M^+$, $-SO_3H$, $-CH_2C(O)O^-M^+$, $-CH_2C(O)OH$;
- and $M^+$ is a cation.

6. The composition of claim 5, wherein m is from 2 to 15.

7. The composition of claim 5, wherein n is from 0 to 10.

8. The composition of claim 5, wherein m is an integer from 3 to 10 and n is an integer from 0 to 10, and wherein m+n is from 3 to 15.

9. The composition of claim 5, wherein $R^1$ is a branched $C_7$-$C_{12}$ alkyl group.

10. The composition of claim 5, wherein $R^1$ is a 2-ethylhexyl group.

11. The composition of claim 1, wherein the additional surfactant comprises an anionic surfactant selected from the group consisting of alkoxy carboxylate surfactants, alkoxy sulfate surfactants, alkoxy sulfonate surfactants, alkyl sulfonate surfactants, aryl sulfonate surfactants, olefin sulfonate surfactants, and combinations thereof.

12. The composition of claim 1, wherein the additional surfactant is present in the composition in an amount of from 0.05% to 2% by weight, based on the total weight of the composition.

13. The composition of claim 1, wherein the additional surfactant comprises a $C_{10}$-$C_{30}$ internal olefin sulfate (IOS) or a $C_8$-$C_{30}$ alkyl benzene sulfonate (ABS).

14. The composition of claim 1, wherein the additional surfactant comprises an alkoxy carboxylate surfactant defined by Formula III or Formula IV

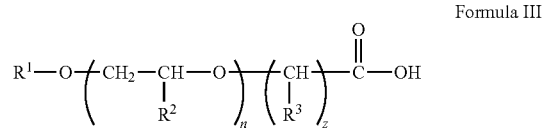

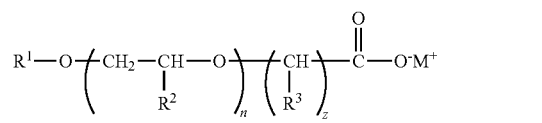

wherein
- $R^1$ substituted or unsubstituted $C_8$-$C_{150}$ alkyl or substituted or unsubstituted aryl;
- $R^2$ is independently hydrogen or unsubstituted $C_1$-$C_6$ alkyl;
- $R^3$ is independently hydrogen or unsubstituted $C_1$-$C_6$ alkyl;
- n is an integer from 2 to 210;
- z is an integer from 1 to 6; and
- $M^+$ is a cation.

15. The composition of claim 1, wherein the additional surfactant comprises an alkoxy sulfate surfactant defined by the formula below

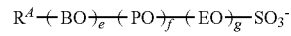

or acid or salt thereof, wherein
- $R^4$ is $C_8$-$C_{36}$ alkyl group;
- BO represents $-CH_2-CH(ethyl)-O-$;
- PO represents $-CH_2-CH(methyl)-O-$;
- EO represents $-CH_2-CH_2-O-$; and
- e, f and g are each independently integers from 0 to 50, with the proviso that at least one of e, f and g is not zero.

16. The composition of claim 1, wherein the additional surfactant comprises an alkoxy sulfate surfactant defined Formula VI

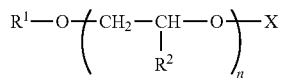

Formula VI wherein
- $R^1$ is an $R^4$-substituted or unsubstituted $C_8$-$C_{20}$ alkyl group, an $R^3$-substituted or unsubstituted aryl group, or an $R^3$-substituted or unsubstituted cycloalkyl group;
- $R^2$ is independently hydrogen or methyl;
- $R^3$ is independently an $R^4$-substituted or unsubstituted $C_1$-$C_{15}$ alkyl, an $R^4$-substituted or unsubstituted aryl group, or an $R^4$-substituted or unsubstituted cycloalkyl group;
- $R^4$ is independently an unsubstituted aryl group or an unsubstituted cycloalkyl group;
- n is an integer from 25 to 115;
- X is $-SO_3^-M^+$, $-SO_3H$, $-CH_2C(O)O^-M^+$, $-CH_2C(O)OH$; and
- $M^+$ is a cation.

17. The composition of claim 1, wherein the composition comprises
(i) 0.05% to 1% by weight of the compound of Formula I;
(ii) 0.05% to 1% by weight of a $C_{10}$-$C_{30}$ internal olefin sulfate (IOS) or a $C_8$-$C_{30}$ alkyl benzene sulfonate (ABS); and
(iii) 0.05% to 1% by weight an alkoxy sulfate surfactant defined by the formula below

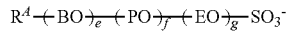

or acid or salt thereof, wherein
- $R^A$ is $C_8$-$C_{36}$ alkyl group;
- BO represents $-CH_2-CH(ethyl)-O-$;
- PO represents $-CH_2-CH(methyl)-O-$;
- EO represents $-CH_2-CH_2-O-$; and
- e, f and g are each independently integers from 0 to 50, with the proviso that at least one of e, f, and g is not zero.

18. The composition of claim 1, wherein the composition includes the polymer.

19. The composition of claim 1, wherein the composition includes the alkali agent.

20. The composition of claim 1, wherein the composition has a pH of from 10 to 12.

21. The composition of claim 1, wherein the composition is substantially free of co-solvents.

22. The composition of claim 1, wherein the composition has a salinity of at least 5,000 ppm.

23. The composition of claim 1, wherein the polymer is present and is selected from polyacrylamide, a partially hydrolyzed polyacrylamide, a copolymer of 2-acrylamido-2-methylpropane sulfonic acid or sodium salt and polyacrylamide, or a combination thereof.

24. An emulsion comprising (i) an aqueous composition according to claim 1
(ii) unrefined petroleum, and
(iii) an additional surfactant.

25. A method of displacing an unrefined petroleum material in contact with a solid material, said method comprising:
(i) contacting the unrefined petroleum material with a composition comprising an aqueous composition according to claim 1,
wherein the unrefined petroleum material is in contact with the solid material; and
(ii) allowing the unrefined petroleum material to separate from the solid material, thereby displacing the unrefined petroleum material in contact with the solid material.

* * * * *